United States Patent
Shimizu et al.

(10) Patent No.: US 8,173,348 B2
(45) Date of Patent: May 8, 2012

(54) METHOD OF FORMING PATTERN AND COMPOSITION FOR FORMING OF ORGANIC THIN-FILM FOR USE THEREIN

(75) Inventors: Daisuke Shimizu, Tokyo (JP); Hikaru Sugita, Tokyo (JP); Nobuji Matsumura, Tokyo (JP); Toshiyuki Kai, Tokyo (JP); Tsutomu Shimokawa, Tokyo (JP)

(73) Assignee: JSR Corporation, Tokyo (JP)

( * ) Notice: Subject to any disclaimer, the term of this patent is extended or adjusted under 35 U.S.C. 154(b) by 549 days.

(21) Appl. No.: 12/305,893

(22) PCT Filed: Jun. 21, 2007

(86) PCT No.: PCT/JP2007/062538
§ 371 (c)(1),
(2), (4) Date: Dec. 19, 2008

(87) PCT Pub. No.: WO2008/001679
PCT Pub. Date: Jan. 3, 2008

(65) Prior Publication Data
US 2010/0233635 A1    Sep. 16, 2010

(30) Foreign Application Priority Data

Jun. 27, 2006    (JP) ................................. 2006-177034
Sep. 29, 2006   (JP) ................................. 2006-268671

(51) Int. Cl.
*G03F 7/00* (2006.01)
*G03F 7/004* (2006.01)
*G03F 7/075* (2006.01)
*G03F 7/40* (2006.01)

(52) U.S. Cl. .................. 430/270.1; 430/312; 430/273.1; 430/330; 430/331

(58) Field of Classification Search ............... 430/270.1, 430/312, 273.1, 330, 331
See application file for complete search history.

(56) References Cited

U.S. PATENT DOCUMENTS

| | | | |
|---|---|---|---|
| 4,945,028 A | 7/1990 | Ogawa | |
| 6,265,135 B1 | 7/2001 | Kodama et al. | |
| 6,576,400 B1 | 6/2003 | Tamura | |
| 6,730,453 B2 * | 5/2004 | Nakashima et al. | 430/270.1 |
| 6,926,953 B2 * | 8/2005 | Nealey et al. | 428/220 |
| 7,098,294 B2 * | 8/2006 | McCullough et al. | 528/377 |
| 7,109,311 B2 * | 9/2006 | Ohsawa et al. | 534/558 |
| 7,244,549 B2 * | 7/2007 | Iwasawa et al. | 430/326 |
| 7,290,350 B2 * | 11/2007 | Lee | 33/640 |
| 7,452,958 B2 * | 11/2008 | McCullough et al. | 528/73 |
| 7,501,223 B2 * | 3/2009 | Takeda et al. | 430/270.1 |
| 2004/0048200 A1 | 3/2004 | Ishibashi | |
| 2007/0248911 A1 * | 10/2007 | Iwasawa et al. | 430/270.1 |
| 2008/0075950 A1 | 3/2008 | Imada et al. | |
| 2008/0096134 A1 * | 4/2008 | Sugimoto et al. | 430/287.1 |
| 2009/0186234 A1 * | 7/2009 | Colburn et al. | 428/500 |
| 2009/0269697 A1 * | 10/2009 | Kato et al. | 430/270.1 |
| 2010/0009286 A1 * | 1/2010 | Takeda et al. | 430/270.1 |

FOREIGN PATENT DOCUMENTS

| | | |
|---|---|---|
| EP | 0588544 | 3/1994 |
| EP | 1684118 A1 * | 7/2006 |
| EP | 1783551 A2 * | 5/2007 |
| GB | 2336845 | 11/1999 |
| JP | 62-293242 | 12/1987 |
| JP | 4-149441 | 5/1992 |
| JP | 6-194842 | 7/1994 |
| JP | 7-252440 | 10/1995 |
| JP | 11-29612 | 2/1999 |
| JP | 2000-21817 | 1/2000 |
| JP | 2000-147777 | 5/2000 |
| JP | 2000143812 A * | 5/2000 |
| JP | 2000-187330 | 7/2000 |
| JP | 2001-23971 | 1/2001 |
| JP | 2001-75283 | 3/2001 |
| JP | 2002-72483 | 3/2002 |
| JP | 2002-107920 | 4/2002 |
| JP | 2005-281283 | 10/2005 |
| WO | WO 2006/016483 | 2/2006 |

OTHER PUBLICATIONS

Extended European Search Report for corresponding EP Application No. 07767364.8-1226, Nov. 3, 2010.

* cited by examiner

*Primary Examiner* — Amanda C. Walke
(74) *Attorney, Agent, or Firm* — Ditthavong Mori & Steiner, P.C.

(57) ABSTRACT

A method for forming a pattern contains (1) a step of forming an underlayer film containing (A) a radiation-sensitive acid generator capable of generating an acid upon exposure to radiation rays or (B) a radiation-sensitive base generator capable of generating a base upon exposure to radiation rays on a substrate; (2) a step of irradiating the underlayer film with radiation rays through a mask with a predetermined pattern to obtain an exposed underlayer film portion having been selectively exposed through the predetermined pattern; (3) a step of forming (C) an organic thin film on the underlayer film so as to attain chemical bonding of the exposed underlayer film portion with the organic thin-film formed on the exposed underlayer film portion; and (4) a step of removing the organic thin film formed on areas of the underlayer film other than the exposed underlayer film portion.

5 Claims, No Drawings

METHOD OF FORMING PATTERN AND COMPOSITION FOR FORMING OF ORGANIC THIN-FILM FOR USE THEREIN

TECHNICAL FIELD

The present invention relates to a method for forming a pattern suitable for microfabrication and a composition for forming an organic thin film used for the method. More particularly, the present invention relates to a method for forming a negative-tone pattern suitable for forming micro-patterns using electron beams (EB), X rays, or extreme ultraviolet radiation (EUV), and to a composition for forming an organic thin film used for the method.

BACKGROUND ART

In the field of microfabrication represented by fabrication of IC chips, the design rules have become more and more stringent in order to achieve higher integration of the circuits. Development of a lithographic process enabling microfabrication in a stable manner has been actively pursued. However, since it has been difficult to form micro patterns of 22 nm or less with high precision by a general method of using KrF or ArF excimer lasers, a method of using EB or EUV has been proposed.

As a radiation-sensitive resin composition used for a positive-tone resist agent using EB or EUV for use in ultra-microfabrication, (1) a chemically amplified radiation-sensitive resin composition containing a polyhydroxystyrene resin partially protected by an acid-dissociable functional group (a resin for KrF excimer), a novolak resin (a resin for i-lines), and an acid generator and (2) a methacryl main chain cut-type radiation-sensitive resin composition containing PMMA (polymethyl methacrylate) and the like have been disclosed.

As specific examples of the composition (1), a composition containing a polyhydroxystyrene resin partially protected by an acetal group and an acid generator having well-balanced high sensitivity, high resolution, and high etching resistance (see Patent Document 1), a composition containing polyhydroxystyrene resin partially protected by various acid dissociable groups, an onium salt which generates a fluorine-containing aromatic sulfonic acid, and a fluorine-containing or silicon-containing surfactant (see Patent Document 2), an onium salt having at least one electron attractive group (a fluorine, a cyano group, a nitro group, etc.) as a substituent of a cation moiety (see Patent Document 3), a resin having a disulfonyl group (see Patent Document 4), a resin having an N-oxyimidesulfonyl group (see Patent Document 5), and the like have been disclosed. However, these methods have not still reached a practical use level in surface roughness during micro-pattern formation, sensitivity, and resolution.

On the other hand, the methacryl main chain cut-type radiation-sensitive resin composition (2) is excellent in resolution, but has problems in etching resistance, sensitivity, and outgassing. Therefore, it is difficult to use this resin composition in practice. In addition to these compositions, poly-t-butyl-α-chloromethylstyrene excellent in balance of resolution and sensitivity (Patent Document 6) and a resin with an atom (N, O, S) which is cut with ease by electron beams introduced into the resin terminal (Patent Document 7) have been disclosed. However, although some improvement may be recognized in sensitivity, the resins still have problems in sensitivity, etching resistance, and outgassing. These resins therefore have not yet reached a practically usable level.
[Patent Document 1] JP-A-6-194842
[Patent Document 2] JP-A-2000-187330
[Patent Document 3] JP-A-2001-075283
[Patent Document 4] JP-A-2002-072483
[Patent Document 5] JP-A-2002-107920
[Patent Document 6] JP-A-2000-147777
[Patent Document 7] JP-A-11-29612

DISCLOSURE OF THE INVENTION

The present invention has been achieved in view of the above-mentioned problems in general technologies. An object of the present invention is to provide a method for forming a pattern having excellent etching resistance and resolution, being expected to reduce outgassing, and capable of forming micro patterns with high precision, as well as a composition for forming an organic thin film used for the method.

According to the present invention, the following methods for forming a pattern and compositions for forming an organic thin film are provided.

[1] A method for forming a pattern, comprising; (1) a step of forming on a substrate an underlayer film containing (A) a radiation-sensitive acid generator capable of generating an acid upon exposure to radiation rays or (B) a radiation-sensitive base generator capable of generating a base upon exposure to radiation rays on a substrate; (2) a step of irradiating the underlayer film with radiation rays through a mask with a predetermined pattern to obtain an exposed underlayer film portion having been selectively exposed to radiation rays through the predetermined pattern; (3) a step of forming (C) an organic thin film on the underlayer film so as to attain chemical bonding of the exposed underlayer film portion to the organic thin film formed on the exposed underlayer film portion; and (4) a step of removing the organic thin film formed on areas of the underlayer film other than the exposed underlayer film portion.

[2] The method for forming a pattern according to [1], wherein the underlayer film further contains at least one hydrolyzate and/or condensate selected from the group consisting of (D) a compound (D-1) shown by the following formula (1) and a compound (D-2) shown by the following formula (2), $$R^1_a Si(OR^2)_{4-a} \quad (1)$$

wherein $R^1$ represents a hydrogen atom, a fluorine atom, or a monovalent organic group, $R^2$ represents a monovalent organic group, and a represents an integer of 0 to 2, $$R^3_b(R^4O)_{3-b}Si\text{—}(R^7)_d\text{—}Si(OR^5)_{3-c}R^6_c \quad (2)$$

wherein $R^3$ to $R^6$ may be the same or different and each represents a substituted or unsubstituted alkyl group, aryl group, allyl group, or glycidyl group, b and c may be the same or different and represent an integer of 0 to 2, $R^7$ represents an oxygen atom or a "—$(CH_2)_n$—"-bond, d represents 0 or 1, and n represents an integer of 1 to 6.

[3] The method for forming a pattern according to [1], wherein the underlayer film further contains (E) a polymer which has at least one repeating unit selected from the group consisting of (E-1) a repeating unit shown by the following formula (3) and (E-2) a repeating unit shown by the following formula (4), and has a polystyrene-reduced weight average molecular weight (Mw) measured by the gel-permeation chromatography method of 500 to 500,000,

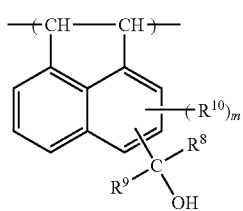

(3)

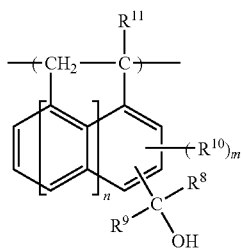

(4)

wherein $R^8$ and $R^9$ individually represent a hydrogen atom, an alkyl group having 1 to 3 carbon atoms, or an aryl group, $R^{10}$ represents an alkyl group having 1 to 3 carbon atoms, a vinyl group, an allyl group, or an aryl group, $R^{11}$ represents a hydrogen atom or a methyl group, n represents 0 or 1, and m represents an integer of 0 to 2.

[4] The method for forming a pattern according to [1], wherein the underlayer film further contains (F) a polymer which has a repeating unit shown by the following formula (5) and has a polystyrene-reduced weight average molecular weight (Mw) measured by the gel-permeation chromatography method of 500 to 500,000,

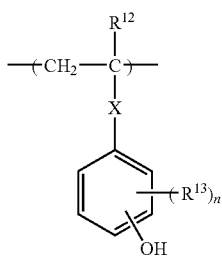

(5)

wherein $R^{12}$ represents a hydrogen atom or a methyl group, $R^{13}$ represents an alkyl group having 1 to 3 carbon atoms, a vinyl group, an allyl group, or an aryl group, X represents a single bond, —C(=O)—O—, or —C(=O)—NH—, and n represents an integer of 0 to 4.

[5] The method for forming a pattern according to any one of [1] to [4], wherein the organic thin film contains an oligothiophene derivative.

[6] The method for forming a pattern according to [5], wherein the oligothiophene derivative contains an acid-dissociable group or a base-dissociable group.

[7] The method for forming a pattern according to [6], wherein the acid-dissociable group contained in the oligothiophene derivative is shown by the following formula (6), —Si(OR$^{14}$)$_3$     (6)

wherein $R^{14}$s may be the same or different and each independently represents a substituted or unsubstituted alkyl group having 1 to 5 carbon atoms, an aryl group having 6 to 14 carbon atoms, an allyl group, a glycidyl group, or a hydrogen atom.

[8] A composition for forming (C) an organic thin film used in the method for forming a pattern according to any one of [1] to [7], comprising (G) an oligothiophene derivative and (H) a solvent.

According to the method for forming a pattern of the present invention, micro patterns can be formed at a high precision. The method for forming a pattern of the present invention excels in etching resistance and resolution, and is expected to reduce outgassing.

In addition, the composition for forming an organic thin film of the present invention can be suitably used for the method of forming a pattern of the present invention. Therefore, micro patterns can be formed at a high precision by using the composition for forming an organic thin film of the present invention.

BEST MODE FOR CARRYING OUT THE INVENTION

The preferred embodiments for carrying out the present invention are described below. However, the present invention is not restricted to the following embodiments and it should be construed that there are also included, in the present invention, those embodiments in which appropriate changes, improvements, etc. have been made to the following embodiments based on the ordinary knowledge possessed by those skilled in the art, as long as there is no deviation from the gist of the present invention.

An embodiment of the method for forming a pattern of the present invention comprises (1) a step of forming an underlayer film containing (A) a radiation-sensitive acid generator capable of generating an acid upon exposure to radiation rays or (B) a radiation-sensitive base generator capable of generating a base upon exposure to radiation rays on a substrate (hereinafter referred to from time to time as a "first step"); (2) a step of irradiating the underlayer film with radiation rays through a mask with a predetermined pattern to obtain an exposed underlayer film portion having been selectively exposed through the predetermined pattern (hereinafter referred to from time to time as a "second step"); (3) a step of forming (C) an organic thin film on the underlayer film so as to attain chemical bonding of the exposed underlayer film portion to the organic thin film formed on the exposed underlayer film portion (hereinafter referred to from time to time as a "third step"); and (4) a step of removing the organic thin film formed on areas of the underlayer film other than the exposed underlayer film portion (hereinafter referred to from time to time as a "fourth step"). The details are described below.

1. First Step:

The first step comprises forming an underlayer film containing (A) a radiation-sensitive acid generator capable of generating an acid upon exposure to radiation rays (hereinafter, referred to from time to time as "photoacid generator" or "component (A)") or (B) a radiation-sensitive base generator capable of generating a base upon exposure to radiation rays (hereinafter, referred to from time to time as "photobase generator" or "component (B)") on a substrate.

As the substrate, a silicon wafer, a wafer covered with aluminum, and the like may be used. The underlayer film may be formed on the substrate by applying the composition for forming the underlayer film containing the component (A) or the component (B) in the form of a film and drying the film.

The composition for forming the underlayer film may be applied by an appropriate method such as rotation application, cast coating, and roll coating. The film is cured by heating to form the underlayer film. The heating temperature is generally from about 90 to 350° C., and preferably from about 200 to 300° C. The thickness of the underlayer film is generally 0.1 to 5

(Underlayer Film Composition)

The underlayer film composition is a composition which can be used for forming an underlayer film. The composition of the underlayer film contains the component (A) or the component (B).

(Radiation-Sensitive Acid Generating Agent (A))

As the component (A), a compound which generates an acid by ultraviolet radiation with an energy of 1 to 100 mJ, preferably 10 to 50 mJ is used. The following compounds can be given as preferable examples of the component (A).

onium salt photoacid generators such as diphenyliodonium trifluoromethanesulfonate, diphenyliodonium dodecylbenzenesulfonate, diphenyliodonium nonafluoro-n-butanesulfonate, bis(4-t-butylphenyl)iodonium trifluoromethanesulfonate, bis(4-t-butylphenyl)iodonium dodecylbenzenesulfonate, bis(4-t-butylphenyl)iodonium naphthalenesulfonate, bis(4-t-butylphenyl)iodonium nonafluoro-n-butanesulfonate, triphenylsulfonium trifluoromethanesulfonate, triphenylsulfonium naphthalenesulfonate, triphenylsulfonium nonafluoro-n-butanesulfonate, diphenyl(4-methylphenyl)sulfonium trifluoromethanesulfonate, diphenyl(4-methoxyphenyl)sulfonium trifluoromethanesulfonate, (hydroxyphenyl)benzenemethylsulfonium toluenesulfonate, cyclohexylmethyl(2-oxocyclohexyl)sulfonium trifluoromethanesulfonate, dicyclohexyl(2-oxocyclohexyl)sulfonium trifluoromethanesulfonate, dimethyl(2-oxocyclohexyl)sulfonium trifluoromethanesulfonate, triphenylsulfonium camphorsulfonate, (4-hydroxyphenyl)benzylmethylsulfonium toluenesulfonate, 1-naphtyldimethylsulfonium trifluoromethanesulfonate, 1-naphtyldiethylsulfonium trifluoromethanesulfonate, 4-cyano-1-naphtyldimethylsulfonium trifluoromethanesulfonate, 4-nitro-1-naphtyldimethylsulfonium trifluoromethanesulfonate, 4-methyl-1-naphtyldimethylsulfonium trifluoromethanesulfonate, 4-cyano-1-naphtyldiethylsulfonium trifluoromethanesulfonate, 4-nitro-1-naphtyldiethylsulfonium trifluoromethanesulfonate, 4-methyl-1-naphtyldiethylsulfonium trifluoromethanesulfonate, 4-hydroxy-1-naphtyldimethylsulfonium trifluoromethanesulfonate, 4-hydroxy-1-naphthyltetrahydrothiophenium trifluoromethanesulfonate, 4-methoxy-1-naphthyltetrahydrothiophenium trifluoromethanesulfonate, 4-ethoxy-1-naphthyltetrahydrothiophenium trifluoromethanesulfonate, 4-methoxymethoxy-1-naphthyltetrahydrothiophenium trifluoromethanesulfonate, 4-ethoxymethoxy-1-naphthyltetrahydrothiophenium trifluoromethanesulfonate, 4-(1-methoxyethoxy)-1-naphthyltetrahydrothiophenium trifluoromethanesulfonate, 4-(2-methoxyethoxy)-1-naphthyltetrahydrothiophenium trifluoromethanesulfonate, 4-methoxycarbonyloxy-1-naphthyltetrahydrothiophenium trifluoromethanesulfonate, 4-ethoxycarbonyloxy-1-naphthyltetrahydrothiophenium trifluoromethanesulfonate, 4-n-propoxycarbonyloxy-1-naphthyltetrahydrothiophenium trifluoromethanesulfonate, 4-i-propoxycarbonyloxy-1-naphthyltetrahydrothiophenium trifluoromethanesulfonate, 4-n-butoxycarbonyloxy-1-naphthyltetrahydrothiophenium trifluoromethanesulfonate, 4-t-butoxycarbonyloxy-1-naphthyltetrahydrothiophenium trifluoromethanesulfonate, 4-(2-tetrahydrofuranyloxy)-1-naphthyltetrahydrothiophenium trifluoromethanesulfonate, 4-(2-tetrahydropyranyloxy)-1-naphthyltetrahydrothiophenium trifluoromethanesulfonate, 4-benzyloxy-1-naphthyltetrahydrothiophenium trifluoromethanesulfonate, and 1-(naphthylacetomethyl)tetrahydrothiophenium trifluoromethanesulfonate;

halogen-containing compound photoacid generators such as phenylbis(trichloromethyl)-s-triazine and naphthylbis(trichloromethyl)-s-triazine;

diazoketone compound photoacid generators such as 1,2-naphthoquinonediazido-4-sulfonylchloride, 1,2-naphthoquinonediazido-5-sulfonylchloride, 1,2-naphthoquinonediazido-4-sulfonate of 2,3,4,4'-tetrabenzophenone, and 1,2-naphthoquinonediazido-5-sulfonate of 2,3,4,4'-tetrabenzophenone; sulfonic acid compound photoacid generators such as 4-trisphenacylsulfone, mesitylphenacylsulfone, and bis(phenylsulfonyl)methane; and a sulfonic acid compound photoacid generator such as benzointosylate, tris(trifluoromethanesulfonate) of pyrogallol, nitrobenzyl-9,10-diethoxyanthracene-2-sulfonate, trifluoromethanesulfonyl bicyclo[2,2,1]hept-5-ene-2,3-dicarbodiimide, N-hydroxysuccinimide trifluoromethanesulfonate, 1,8-naphthalenedicarboxylic acid imide trifluoromethanesulfonate. These components (A) can be used individually or in combination of two or more.

(Radiation-Sensitive Base Generator (B))

The following compounds can be given as preferable examples of the component (B):
2-hydroxy-2-phenylacetophenone-N-cyclohexylcarbamate $((C_6H_5C(=O)CH(C_6H_5)OC(=O)NHC_6H_{11}))$, o-nitrobenzyl-N-cyclohexylcarbamate $(o-NO_2C_6H_5CH_2OC(=O)NHC_6H_{11})$, N-cyclohexyl-2-naphthalenesulfonamide $(C_{10}H_7SO_2NHC_6H_{11})$, 3,5-dimethoxybenzyl-N-cyclohexylcarbamate $((CH_3O)_2C_6H_5CH_2OC(=O)NHC_6H_{11})$, N-cyclohexyl-p-toluenesulfonamide $(p-CH_3C_6H_5SO_2NHC_6H_{11})$, dibenzoinisophoronedicarbamate, [[(2-nitrobenzyl)oxy]carbonyl]cyclohexylamine, N-[[(2-nitrophenyl)-1-methylmethoxy]carbonyl]cyclohexylamine, N-[[(2,6-dinitrophenyl)-1-methylmethoxy]carbonyl]cyclohexylamine, N-[[(2-nitrophenyl)-1-(2'-nitrophenyl)methoxy]carbonyl]cyclohexylamine, N-[[(2,6-dinitrophenyl)-1-(2',6'-dinitrophenyl)methoxy]carbonyl]cyclohexylamine, 2-nitrobenzyl cyclohexylcarbamate, 1-(2-nitrophenyl)ethyl cyclohexylcarbamate, 2,6-dinitrobenzyl cyclohexylcarbamate, 1-(2,6-dinitrophenyl)ethyl cyclohexylcarbamate, 1-(3,5-dimethoxyphenyl)-1-methylethyl cyclohexylcarbamate, 1-benzoyl-1-phenylmethyl cyclohexylcarbamate, 2-benzoyl-2-hydroxy-2-phenylethyl cyclohexylcarbamate, 1,2,3-benzenethyl tris(cyclohexylcarbamate), α-(cyclohexylcarbamoyloxyimino)-α-(4-methoxyphenyl)acetonitrile, N-(cyclohexylcarbamoyloxy)succinimide, the compounds shown by the following formulas (7-1) to (7-3), (8-1) to (8-5), (9-1), (9-2), (10-1) to (10-4), (11-1) to (11-4), (12-1) to (12-3), and (13-1) to (13-5),

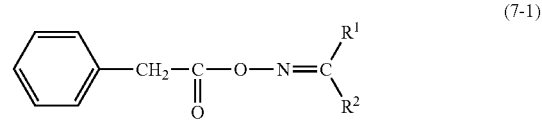

(7-1)

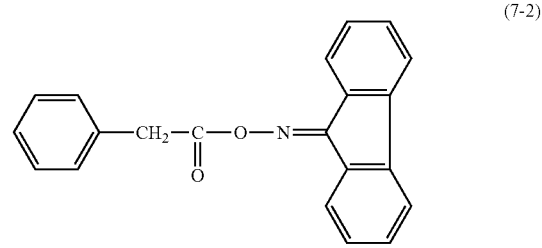

(7-2)

-continued

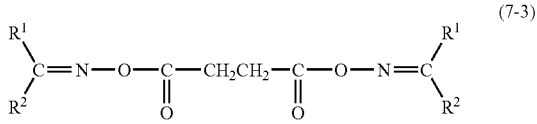
(7-3)

wherein, in the formulas (7-1) to (7-3), $R^2$ to $R^6$ individually represent a methyl group, a phenyl group, or a naphthyl group,

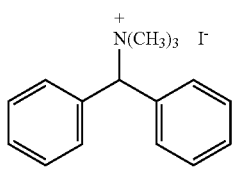
(8-1)

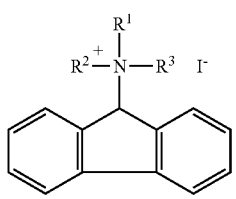
(8-2)

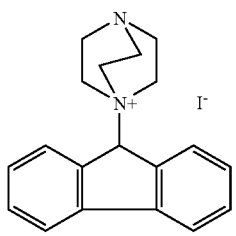
(8-3)

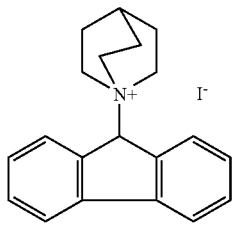
(8-4)

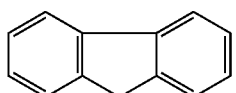
(8-5)

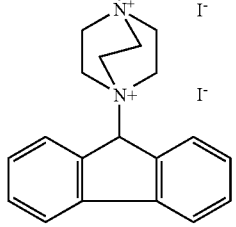

wherein, in the formula (8-2), $R^1$ to $R^3$ individually represent a methyl group or an ethyl group,

(9-1)

(9-2)

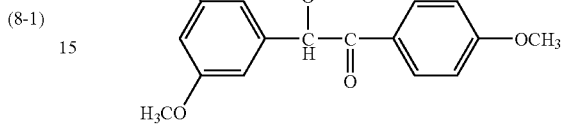

wherein, in the formula (9-1), $R^1$ to $R^3$ individually represent a phenyl group, a 3,5-dimethoxyphenyl group, a 4-methoxyphenyl group, a naphthyl group, or a 4-thiomethylphenyl group,

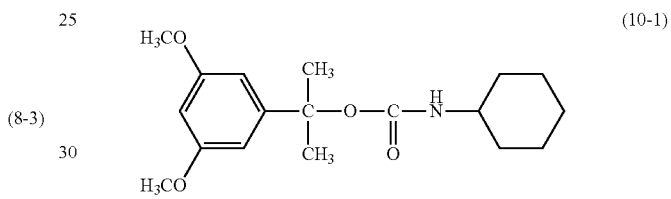
(10-1)

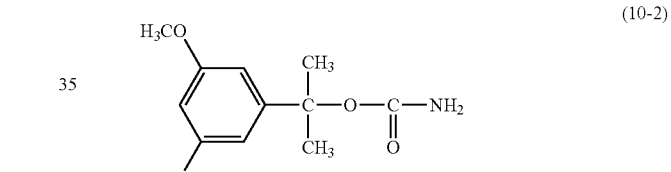
(10-2)

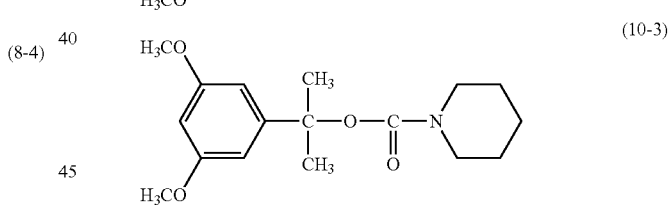
(10-3)

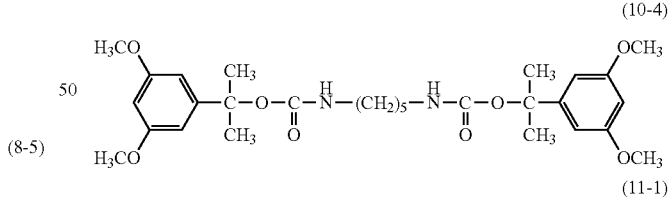
(10-4)

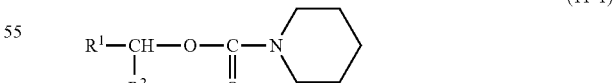
(11-1)

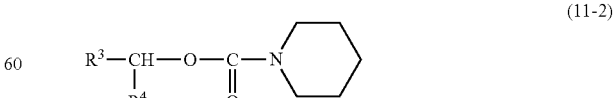
(11-2)

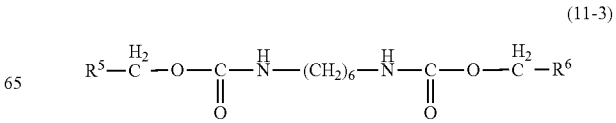
(11-3)

(11-4)

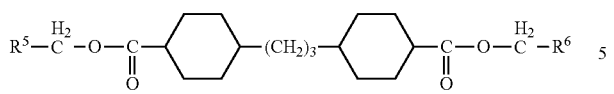

wherein, in the formula (11-1), $R^1$ and $R^2$ individually represent a hydrogen atom, a 2-nitrophenyl group, or a 2,6-dinitrophenyl group, provided that $R^1$ and $R^2$ are not a hydrogen atom at the same time, in the formula (11-2), $R^3$ represents a 2-nitrophenyl group, a 2,6-dinitrophenyl group, or a 2,4-dinitrophenyl group, and $R^4$ represents a hydrogen atom or a methyl group, and in the formulas (11-3) and (11-4), $R^5$ and $R^6$ individually represent a 2-nitrophenyl group or a 2,6-dinitrophenyl group, (12-1)

[Co(NH$_3$)$_5$Br](ClO$_4$)$_2$ (12-2)

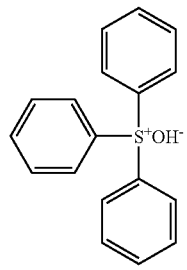

(12-3)

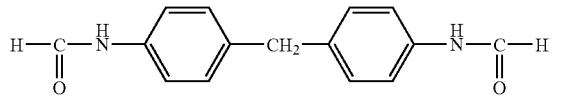

(13-1)

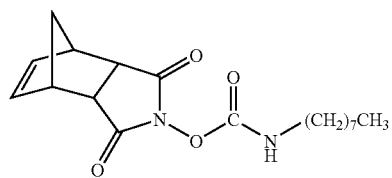

(13-2)

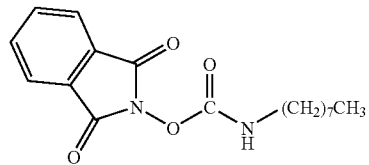

(13-3)

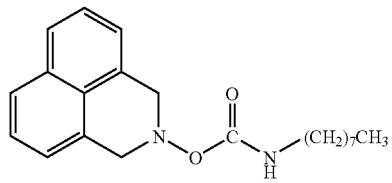

(13-4)

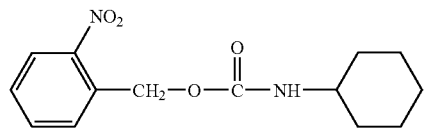

(13-5)

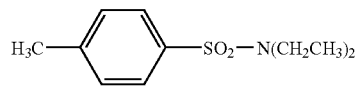

and the compounds shown by the following formula (14), (14)

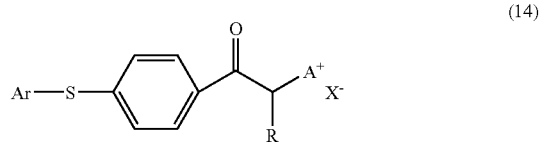

wherein, in the formula (14), Ar represents a substituted or unsubstituted phenyl, biphenyl, naphthyl, or 4-(phenylthio)phenyl, and R represents a hydrogen or a $C_1$ to $C_{18}$ alkyl. In the above formula (14), wherein Ar is an alkyl group having 1 to 18 carbon atoms, an alkenyl group having 3 to 18 carbon atoms, an alkynyl group having 3 to 18 carbon atoms, a haloalkyl group having 1 to 18 carbon atoms, $NO_2$, OH, CN, $OR^1$, $SR^2$, $C(O)R^3$, or $C(O)OR^4$ (wherein $R^1$, $R^2$, $R^3$, and $R^4$ are hydrogen atoms or alkyl groups having 1 to 18 carbon atoms). These groups represented by Ar may be mono- or poly-substituted with halogen, provided that Ar is preferably a substituted or unsubstituted phenyl, and more preferably an unsubstituted phenyl. In the formula (14), R represents preferably a hydrogen atom or an alkyl group having 1 to 18 carbon atoms, more preferably a hydrogen atom or an alkyl group having 1 to 3 carbon atoms, and particularly preferably a hydrogen atom.

In the formula (14), $A^+$ represents any of ammonium ions shown by the following formulas (15-1) to (15-5), preferably an ammonium ion shown by the following formulas (15-1) to (15-3).

(15-1)

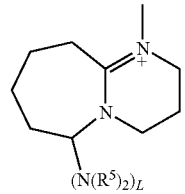

(15-2)

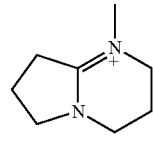

(15-3)

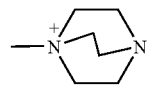

(15-4)

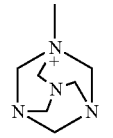

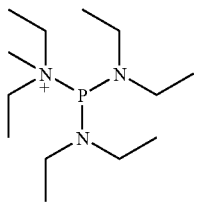
(15-5)

In the formula (15-1), L represents 1 or 0, and $R^5$ represents an alkyl group having 1 to 5 carbon atoms. L represents preferably 0. In the formula (14), $X^-$ represents a counter anion of $A^+$. As specific examples of $X^-$, a borate anion, an N,N-dimethyldithiocarbamate anion, an N,N-dimethylcarbamate anion, a thiocyanate anion, or a cyanate anion can be given. Of these, the borate anion is preferable. As specific examples of the borate anion, tetraphenyl borate, methyltriphenyl borate, ethyltriphenyl borate, propyltriphenyl borate, butyltriphenyl borate, pentyltriphenyl borate, and hexyltributyl borate can be given.

The compound shown by the formula (14) is decomposed by absorbing an ultraviolet radiation with a comparatively long wavelength (300 nm or more) and generates a strong base shown by the following formulas (16-1) to (16-5) (e.g. 1,8-diazabicyclo[5,4,0]-7-undecene derivatives, 1,5-diazabicyclo[4,3,0]-5-nonene, triethylenediamine, hexamethylenetetramine, tris(diethylamino)phosphine). The compound shown by the formula (14), therefore, has very high activity to polymerization of an episulfide compound. The above-mentioned compounds of the component (B) can be used individually or in combination of two or more.

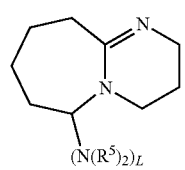
(16-1)

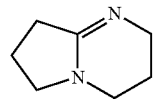
(16-2)

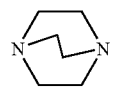
(16-3)

(16-4)

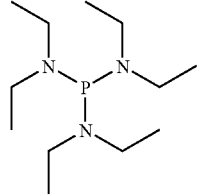
(16-5)

(Hydrolyzate and/or Condensate (D))

It is preferable that the underlayer film composition further contains a hydrolyzate and/or condensate (hereinafter referred to from time to time as "component (D)") in addition to the component (A) and component (B).

The component (D) contains a compound shown by the following formula (1) (hereinafter referred to from time to time as "component (D-1)") and/or a compound shown by the following formula (2) (hereinafter referred to from time to time as "component (D-2)"), $$R^1_a Si(OR^2)_{4-a} \quad (1)$$

wherein, in the formula (1), $R^1$ represents a hydrogen atom, a fluorine atom, or a monovalent organic group, $R^2$ represents a monovalent organic group, and a represents an integer of 0 to 2, $$R^3_b(R^4O)_{3-b}Si-(R^7)_d-Si(OR^5)_{3-c}R^6_c \quad (2)$$

wherein, in the formula (2), $R^3$ to $R^6$ may be the same or different and each represents a substituted or unsubstituted alkyl group, aryl group, allyl group, or glycidyl group, b and c may be the same or different and each represents an integer of 0 to 2, $R^7$ represents an oxygen atom or a "—$(CH_2)_n$—"- bond, d represents 0 or 1, and n represents an integer of 1 to 6.

As examples of the monovalent organic group represented by $R^1$ and $R^2$ in the formula (1), a substituted or unsubstituted alkyl group, aryl group, allyl group, glycidyl group, and the like can be given. $R^1$ in the formula (1) is preferably a monovalent organic group, and particularly preferably an alkyl group or a phenyl group. As the alkyl group, a methyl group, an ethyl group, a propyl group, a butyl group, and the like can be given. Alkyl groups having 1 to 5 carbon atoms are preferable. These alkyl groups may be linear or branched, and may be substituted with a fluorine atom or the like. As examples of the aryl group, a phenyl group, a naphthyl group, a methylphenyl group, an ethylphenyl group, a chlorophenyl group, a bromophenyl group, a fluorophenyl group, and the like can be given.

The following compounds can be given as specific examples of the compound shown by the formula (1).

trimethoxysilane, triethoxysilane, tri-n-propoxysilane, tri-iso-propoxysilane, tri-n-butoxysilane, tri-sec-butoxysilane, tri-tert-butoxysilane, triphenoxysilane, fluorotrimethoxysilane, fluorotriethoxysilane, fluoro-tri-n-propoxysilane, fluorotri-iso-propoxysilane, fluorotri-n-butoxysilane, fluorotri-sec-butoxysilane, fluorotri-tert-butoxysilane, fluorotriphenoxysilane, tetramethoxysilane, tetraethoxysilane, tetra-n-propoxysilane, tetra-iso-propoxysilane, tetra-n-butoxysilane, tetra-sec-butoxysilane, tetra-tert-butoxysilane, tetraphenoxysilane, methyltrimethoxysilane, methyltriethoxysilane, methyltri-n-propoxysilane, methyltri-iso-propoxysilane, methyltri-n-butoxysilane, methyltri-sec-butoxysilane, methyltri-tert-butoxysilane, methyltriphenoxysilane, ethyltrimethoxysilane, ethyltriethoxysilane, ethyltri-n-propoxysilane, ethyltri-iso-propoxysilane, ethyltri-n-butoxysilane, ethyltri-sec-butoxysilane, ethyltri-tert-butoxysilane, ethyltriphenoxysilane, vinyltrimethoxysilane, vinyltriethoxysilane, vinyltri-n-propoxysilane, vinyltri-iso-propoxysilane, vinyltri-n-butoxysilane, vinyltri-sec-butoxysilane, vinyltri-tert-butoxysilane, vinyltriphenoxysilane, n-propyltrimethoxysilane, n-propyltriethoxysilane, n-propyltri-n-propoxysilane, n-propyltri-iso-propoxysilane, n-propyltri-n-butoxysilane, n-propyltri-sec-butoxysilane, n-propyltri-tert-butoxysilane, n-propyltriphenoxysilane, i-propyltrimethoxysilane, i-propyltriethoxysilane, i-propyltri-n-propoxysilane, i-propyltri-iso-propoxysilane, i-propyltri-n-butoxysilane, i-propyltri-sec-butoxysilane, i-propyltri-tert-butoxysilane, i-propyltriphenoxysilane, n-butyltrimethoxysilane, n-butyltriethoxysilane, n-butyltri-n-propoxysilane, n-butyltri-isopropoxysilane, n-butyltri-n-butoxysilane, n-butyltri-sec-butoxysilane, n-butyltri-tert-butoxysilane, n-butyltriphenoxysilane, sec-butyltrimethoxysilane, sec-butyl-i-triethoxysilane, sec-butyltri-n-propoxysilane, sec-butyltri-iso-propoxysilane, sec-butyltri-n-butoxysilane, sec-butyltri-sec-butoxysilane, sec-butyltri-tert-butoxysilane, sec-butyltriphenoxysilane, t-butyltrimethoxysilane, t-butyltriethoxysilane, t-butyltri-n-propoxysilane, t-butyltri-iso-propoxysilane, t-butyltri-n-butoxysilane, t-butyltri-sec-butoxysilane, t-butyltri-tert-butoxysilane, t-butyltriphenoxysilane, phenyltrimethoxysilane, phenyltriethoxysilane, phenyltri-n-propoxysilane, phenyltri-iso-propoxysilane, phenyltri-n-butoxysilane, phenyltri-sec-butoxysilane, phenyltri-tert-butoxysilane, phenyltriphenoxysilane, vinyltrimethoxysilane, vinyltriethoxysilane, γ-aminopropyltrimethoxysilane, γ-aminopropyltriethoxysilane, γ-glycidoxypropyltrimethoxysilane, γ-glycidoxypropyltriethoxysilane, γ-trifluoropropyltrimethoxysilane, γ-trifluoropropyltriethoxysilane, dimethyldimethoxysilane, dimethyldiethoxysilane, dimethyldi-n-propoxysilane, dimethyldi-iso-propoxysilane, dimethyldi-n-butoxysilane, dimethyldi-sec-butoxysilane, dimethyldi-tert-butoxysilane, dimethyldiphenoxysilane, diethyldimethoxysilane, diethyldiethoxysilane, diethyldi-n-propoxysilane, diethyldi-iso-propoxysilane, diethyldi-n-butoxysilane, diethyldi-sec-butoxysilane, diethyldi-tert-butoxysilane, diethyldiphenoxysilane, di-n-propyldimethoxysilane, di-n-propyldiethoxysilane, di-n-propyldi-n-propoxysilane, di-n-propyldi-iso-propoxysilane, di-n-propyldi-n-butoxysilane, di-n-propyldi-sec-butoxysilane, di-n-propyldi-tert-butoxysilane, di-n-propyldi-phenoxysilane, di-iso-propyldimethoxysilane, di-iso-propyldiethoxysilane, di-iso-propyldi-n-propoxysilane, di-iso-propyldi-iso-propoxysilane, di-iso-propyldi-n-butoxysilane, di-iso-propyldi-sec-butoxysilane, di-iso-propyldi-tert-butoxysilane, di-iso-propyldi-phenoxysilane, di-n-butyldimethoxysilane, di-n-butyldiethoxysilane, di-n-butyldi-n-propoxysilane, di-n-butyldi-iso-propoxysilane, di-n-butyldi-n-butoxysilane, di-n-butyldi-sec-butoxysilane, di-n-butyldi-tert-butoxysilane, di-n-butyldi-phenoxysilane, di-sec-butyldimethoxysilane, di-sec-butyldiethoxysilane, di-sec-butyldi-n-propoxysilane, di-sec-butyldi-iso-propoxysilane, di-sec-butyldi-n-butoxysilane, di-sec-butyldi-sec-butoxysilane, di-sec-butyldi-tert-butoxysilane, di-sec-butyldi-phenoxysilane, di-tert-butyldimethoxysilane, di-tert-butyldiethoxysilane, di-tert-butyldi-n-propoxysilane, di-tert-butyldi-iso-propoxysilane, di-tert-butyldi-n-butoxysilane, di-tert-butyldi-sec-butoxysilane, di-tert-butyldi-tert-butoxysilane, di-tert-butyldi-phenoxysilane, diphenyldimethoxysilane, diphenyldi-ethoxysilane, diphenyldi-n-propoxysilane, diphenyldi-iso-propoxysilane, diphenyldi-n-butoxysilane, diphenyldi-sec-butoxysilane, diphenyldi-tert-butoxysilane, diphenyldiphenoxysilane, divinyltrimethoxysilane, γ-aminopropyltrimethoxysilane, γ-aminopropyltriethoxysilane, γ-glycidoxypropyltrimethoxysilane, γ-glycidoxypropyltriethoxysilane, γ-trifluorppropyltriethoxysilane, and γ-trifluorppropyltriethoxysilane.

Among these, tetramethoxysilane, tetraethoxysilane, tetra-n-propoxysilane, tetra-iso-propoxysilane, tetraphenoxysilane, methyltrimethoxysilane, methyltriethoxysilane, methyltri-n-propoxysilane, methyltri-iso-propoxysilane, ethyltrimethoxysilane, ethyltriethoxysilane, vinyltrimethoxysilane, vinyltriethoxysilane, i-propyltrimethoxysilane, i-propyltriethoxysilane, n-butyltrimethoxysilane, n-butyltriethoxysilane, i-butyltrimethoxysilane, i-butyltriethoxysilane, tert-butyltrimethoxysilane, tert-butyltriethoxysilane, phenyltrimethoxysilane, phenyltriethoxysilane, dimethyldimethoxysilane, dimethyldiethoxysilane, diethyldimethoxysilane, diethyldiethoxysilane, diphenyldimethoxysilane, diphenyldiethoxysilane, trimethylmonomethoxysilane, trimethylmonoethoxysilane, triethylmonomethoxysilane, triethylmonoethoxysilane, triphenylmonomethoxysilane, and triphenylmonoethoxysilane are preferable as the compound shown by the formula (1). These compounds can be used individually or in combination of two or more.

Specific examples of the compound in which $R^7$ is an oxygen atom in the formula (2) include hexamethoxydisiloxane, hexaethoxydisiloxane, hexaphenoxydisiloxane, 1,1,1,3,3-pentamethoxy-3-methyldisiloxane, 1,1,1,3,3-pentaethoxy-3-methyldisiloxane, 1,1,1,3,3-pentamethoxy-3-phenyldisiloxane, 1,1,1,3,3-pentaethoxy-3-phenyldisiloxane, 1,1,3,3-tetramethoxy-1,3-dimethyldisiloxane, 1,1,3,3-tetraethoxy-1,3-dimethyldisiloxane, 1,1,3,3-tetramethoxy-1,3-diphenyldisiloxane, 1,1,3,3-tetraethoxy-1,3-diphenyldisiloxane, 1,1,3-trimethoxy-1,3,3-trimethyldisiloxane, 1,1,3-triethoxy-1,3,3-trimethyldisiloxane, 1,1,3-trimethoxy-1,3,3-triphenyldisiloxane, 1,1,3-triethoxy-1,3,3-triphenyldisiloxane, 1,3-dimethoxy-1,1,3,3-tetramethyldisiloxane, 1,3-diethoxy-1,1,3,3-tetramethyldisiloxane, 1,1-dimethoxy-1,1,3,3-tetraphenyldisiloxane, and 1,3-diethoxy-1,1,3,3-tetraphenyldisiloxane. Among these, hexamethoxydisiloxane, hexaethoxydisiloxane, 1,1,3,3-tetramethoxy-1,3-dimethyldisiloxane, 1,1,3,3-tetraethoxy-1,3-dimethyldisiloxane, 1,1,3,3-tetramethoxy-1,3-diphenyldisiloxane, 1,3-dimethoxy-1,1,3,3-tetramethyldisiloxane, 1,3-diethoxy-1,1,3,3-tetramethyldisiloxane, 1,3-dimethoxy-1,1,3,3-tetraphenyldisiloxane, and 1,3-diethoxy-1,1,3,3-tetraphenyldisiloxane are preferable.

Specific examples of the compound in which d is 0 in the formula (2) include hexamethoxydisilane, hexaethoxydisilane, hexaphenoxydisilane, 1,1,1,2,2-pentamethoxy-2-methyldisilane, 1,1,1,2,2-pentaethoxy-2-methyldisilane, 1,1,1,2,2-pentamethoxy-2-phenyldisilane, 1,1,1,2,2-pentaethoxy-2-phenyldisilane, 1,1,2,2-tetramethoxy-1,2-dimethyldisilane, 1,1,2,2-tetraethoxy-1,2-dimethyldisilane, 1,1,2,2-tetramethoxy-1,2-diphenyldisilane, 1,1,2,2-tetraethoxy-1,2-diphenyldisilane, 1,1,2-trimethoxy-1,2,2-trimethyldisilane, 1,1,2-trimethoxy-1,2,2-triphenyldisilane, 1,1,2-triethoxy-1,2,2-trimethyldisilane, 1,1,2-triethoxy-1,2,2-triphenyldisilane, 1,2-dimethoxy-1,1,2,2-tetramethyldisilane, 1,2-diethoxy-1,1,2,2-tetramethyldisilane, 1,2-dimethoxy-1,1,2,2-tetraphenyldisilane, and 1,2-diethoxy-1,1,2,2-tetraphenyldisilane.

Specific examples of the compound in which $R^7$ is "—$(CH_2)_n$—" in the formula (2) include bis(hexamethoxysilyl)methane, bis(hexaethoxysilyl)methane, bis(hexaphenoxysilyl)methane, bis(dimethoxymethylsilyl)methane, bis(diethoxymethylsilyl)methane, bis(dimethoxyphenylsilyl)methane, bis(diethoxyphenylsilyl)methane, bis(methoxydimethylsilyl)methane, bis(ethoxydimethylsilyl)methane, bis(methoxydiphenylsilyl)methane, bis(ethoxydiphenylsilyl)methane, bis(hexamethoxysilyl)ethane, bis(hexaethoxysilyl)ethane, bis(hexaphenoxysilyl)ethane, bis(dimethoxymethylsilyl)ethane, bis(diethoxymethylsilyl)ethane, bis(dimethoxyphenylsilyl)ethane, bis(diethoxyphenylsilyl)ethane, bis(methoxydimethylsilyl)ethane, bis(ethoxydimethylsilyl)ethane, bis(methoxydiphenylsilyl)ethane, bis(ethoxydiphenylsilyl)ethane, 1,3-bis(hexamethoxysilyl)propane, 1,3-bis(hexaethoxysilyl)propane, 1,3-bis (hexaphenoxysilyl)propane, 1,3-bis(dimethoxymethylsilyl)propane, 1,3-bis(diethoxymethylsilyl)propane, 1,3-bis(dimethoxyphenylsilyl)propane, 1,3-bis(diethoxyphenylsilyl)propane, 1,3-bis(methoxydimethylsilyl)propane, 1,3-bis(ethoxydimethylsilyl)propane, 1,3-bis(methoxydiphenylsilyl)propane, and 1,3-bis(ethoxydiphenylsilyl)propane.

As the compound in which d is 0 and $R^7$ is "—$(CH_2)_n$—" in the formula (2), hexamethoxydisilane, hexaethoxydisilane, hexaphenoxydisilane, 1,1,2,2-tetramethoxy-1,2-dimethyldisilane, 1,1,2,2-tetraethoxy-1,2-dimethyldisilane, 1,1,2,2-tetramethoxy-1,2-diphenyldisilane, 1,1,2,2-tetraethoxy-1,2-diphenyldisilane, 1,2-dimethoxy-1,1,2,2-tetramethyldisilane, 1,2-diethoxy-1,1,2,2-tetramethyldisilane, 1,2-dimethoxy-1,1,2,2-tetraphenyldisilane, 1,2-diethoxy-1,1,2,2-tetraphenyldisilane, bis(hexamethoxysilyl)methane, bis(hexaethoxysilyl)methane, bis(dimethoxymethylsilyl)methane, bis(diethoxymethylsilyl)methane, bis(dimethoxyphenylsilyl)methane, bis(diethoxyphenylsilyl)methane, bis(methoxydimethylsilyl)methane, bis(ethoxydimethylsilyl)methane, bis(methoxydiphenylsilyl)methane, and bis(ethoxydiphenylsilyl)methane are preferable.

The component (D) is preferably a hydrolyzate and/or a condensate described in (1) or (2) below. In particular, the hydrolyzate and/or the condensate described in (2) is preferable because of its excellent adhesion to a resist (organic thin film).

(1) A hydrolyzate and/or a condensate shown by the following formula (17),

$$Si(OR^2)_4 \quad (17)$$

wherein, in the formula (17), $R^2$ represents a monovalent organic group. As specific examples of the compound shown by the formula (17), the compounds given as examples of the compound shown by the formula (1) can be given.

(2) A hydrolyzate and/or a condensate of a mixture of silane compounds which include the compound shown by the formula (17) and the compound shown by the following formula (18),

$$R^1{}_n Si(OR^2)_{4-n} \quad (18)$$

wherein, in the formula (18), $R^1$ and $R^2$ may be the same or different and each represents a monovalent organic group, and n represents an integer of 1 to 3. As specific examples of the compound shown by the formula (18), the compounds given as examples of the compound shown by the formula (1) can be given.

When the component (D) is the above hydrolyzate and/or the condensate (2), the content of the compound shown by the formula (18) (as complete hydrolyzed condensate) is preferably 0.5 to 30 parts by mass, and more preferably 0.5 to 25 parts by mass per 100 parts by mass of the compound shown by the formula (17) (as complete hydrolyzed condensate).

To obtain the component (D) by hydrolysis or partial condensation, water is used in an amount of preferably 0.25 to 3 mol, and more preferably 0.3 to 2.5 mol per one mol of the group shown by $R^2O$—, $R^4O$—, or $R^5O$— in the compounds shown by the formulas (1), (2), (17), or (18). If the amount of water used is in the range from 0.25 to 3 mol, homogeneity of the resulting underlayer film tends to decrease and storage stability of the underlayer film composition using for forming the underlayer film tends to be impaired.

The hydrolysis and condensation reactions can be carried out by intermittently or continuously adding water to an organic solvent in which the compound shown by the above formulas (1), (2), (17), and (18) is dissolved. A catalyst is preferably used in hydrolysis and condensation reactions. The catalyst may be previously added to the organic solvent or may be dissolved or dispersed in water during the addition of hydrogenation. The reaction temperature is generally 0 to 100° C., and preferably 15 to 80° C. The underlayer film composition may be obtained by adding an organic solvent and the like to the reaction solution.

When two or more components (D) are used in combination, (a) a mixture of the two or more components may be hydrolyzed and/or (partially) condensed, or (b) the two or more components may be separately hydrolyzed and/or condensed and mixed after the hydrolysis and/or condensation. The method (b) is preferred.

A catalyst is preferably used in the hydrolysis and/or partial condensation. A metal chelate compound, an organic acid, an inorganic acid, an organic base, and an inorganic base can be given as examples of the catalyst.

Specific examples of the metal chelate compound include titanium chelate compounds such as triethoxy mono(acetylacetonate)titanium, tri-n-propoxy mono(acetylacetonate)titanium, tri-t-propoxy mono(acetylacetonate)titanium, tri-n-butoxy mono(acetylacetonate)titanium, tri-sec-butoxy mono(acetylacetonate)titanium, tri-t-butoxy mono(acetylacetonate)titanium, diethoxy bis(acetylacetonate)titanium, di-n-propoxy bis(acetylacetonate)titanium, di-i-propoxy bis(acetylacetonate)titanium, di-n-butoxy bis(acetylacetonate)titanium, di-sec-butoxy bis(acetylacetonate)titanium, di-t-butoxy bis(acetylacetonate)titanium, monoethoxy tris(acetylacetonate)titanium, mono-n-propoxy tris(acetylacetonate)titanium, mono-i-propoxy tris(acetylacetonate)titanium, mono-n-butoxy tris(acetylacetonate)titanium, mono-sec-butoxy tris(acetylacetonate)titanium, mono-t-butoxy tris(acetylacetonate)titanium, tetrakis(acetylacetonate)titanium, triethoxy mono(ethylacetoacetate)titanium, tri-n-propoxy mono(ethylacetoacetate)titanium, tri-i-propoxy mono(ethylacetoacetate)titanium, tri-n-butoxy mono(ethylacetoacetate)titanium, tri-sec-butoxy mono(ethylacetoacetate)titanium, tri-t-butoxy mono(ethylacetoacetate)titanium, diethoxy bis(ethylacetoacetate)titanium, di-n-propoxy bis(ethylacetoacetate)titanium, di-i-propoxy bis(ethylacetoacetate)titanium, di-n-butoxy bis(ethylacetoacetate)titanium, di-sec-butoxy bis(ethylacetoacetate)titanium, di-t-butoxybis(ethylacetoacetate)titanium, monoethoxy tris(ethylacetoacetate)titanium, mono-n-propoxy tris(ethylacetoacetate)titanium, mono-i-propoxy tris(ethylacetoacetate)titanium, mono-n-butoxy tris(ethylacetoacetate)titanium, mono-sec-butoxy tris(ethylacetoacetate)titanium, mono-t-butoxy tris(ethylacetoacetate)titanium, tetrakis(ethylacetoacetate)titanium, mono(acetylacetonate)tris(ethylacetoacetate)titanium, bis(acetylacetonate)bis(ethylacetoacetate)titanium, and tris(acetylacetonate)mono(ethylacetoacetate)titanium;

zirconium chelate compounds such as triethoxy mono(acetylacetonate)zirconium, tri-n-propoxy mono(acetylacetonate)zirconium, tri-i-propoxy mono(acetylacetonate)zirconium, tri-n-butoxy mono(acetylacetonate)zirconium, tri-sec-butoxy mono(acetylacetonate)zirconium, tri-t-butoxy mono(acetylacetonate) zirconium, diethoxy bis(acetylacetonate) zirconium, di-n-propoxy bis(acetylacetonate)zirconium, di-i-propoxy bis(acetylacetonate)zirconium, di-n-butoxy bis(acetylacetonate)zirconium, di-sec-butoxy bis(acetylacetonate)zirconium, di-t-butoxy bis(acetylacetonate)zirconium, mono-ethoxy tris(acetylacetonate)zirconium, mono-n-propoxy tris(acetylacetonate)zirconium, mono-i-propoxy tris(acetylacetonate)zirconium, mono-n-butoxy tris(acetylacetonate)zirconium, mono-sec-butoxy tris(acetylacetonate)

zirconium, mono-t-butoxy tris(acetylacetonate)zirconium, tetrakis(acetylacetonate)zirconium,
triethoxy mono(ethylacetoacetate)zirconium, tri-n-propoxy mono(ethylacetoacetate)zirconium, tri-i-propoxy mono(ethylacetoacetate)zirconium, tri-n-butoxy mono(ethylacetoacetate)zirconium, tri-sec-butoxy mono-(ethylacetoacetate)zirconium, tri-t-butoxy mono(ethylacetoacetate)zirconium, diethoxy bis(ethylacetoacetate)zirconium, di-n-propoxy bis(ethylacetoacetate)zirconium, di-i-propoxy bis(ethylacetoacetate)zirconium, di-n-butoxy bis(ethylacetoacetate)zirconium, di-sec-butoxy bis(ethylacetoacetate)zirconium, di-t-butoxy bis(ethylacetoacetate)zirconium, monoethoxy tris(ethylacetoacetate)zirconium, mono-n-propoxy tris(ethylacetoacetate)zirconium, mono-i-propoxy tris(ethylacetoacetate)zirconium, mono-n-butoxy tris(ethylacetoacetate)zirconium, mono-sec-butoxy tris(ethylacetoacetate)zirconium, mono-t-butoxy tris(ethylacetoacetate)zirconium, tetrakis(ethylacetoacetate) zirconium, mono(acetylacetonate) tris(ethylacetoacetate) zirconium, bis(acetylacetonate) bis(ethylacetoacetate) zirconium, and tris(acetylacetonate) mono(ethylacetoacetate) zirconium;
and aluminum chelate compounds such as tris(acetylacetonate)aluminum and tris(ethylacetoacetate)aluminum.

As specific examples of the organic acids, acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linolic acid, linoleic acid, salicylic acid, benzoic acid, p-aminobenzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, and the like can be given.

As specific examples of the inorganic acid, hydrochloric acid, nitric acid, sulfuric acid, hydrofluoric acid, and phosphoric acid, can be given. As specific examples of the organic base, pyridine, pyrrole, piperazine, pyrrolidine, piperidine, picoline, trimethylamine, triethylamine, monoethanolamine, diethanolamine, dimethyl monoethanolamine, monomethyldiethanolamine, triethanolamine, diazabicyclo octane, diazabicyclo nonane, diazabicyclo undecene, tetramethyl ammonium hydroxide, and the like can be given. As specific examples of the inorganic base, ammonia, sodium hydroxide, potassium hydroxide, barium hydroxide, calcium hydroxide, and the like can be given.

Among these catalysts, a metal chelate compound, an organic acid, and an inorganic acid are preferable, and a titanium chelate compound and an organic acid are more preferable. These catalysts can be used individually or in combination of two or more. The amount of the catalyst used is generally 0.001 to 10 parts by mass, and preferably 0.01 to 10 parts by mass for 100 parts by mass of each of the compounds (as complete hydrolysis condensate) of the above formulas (1), (2), (17), or (18).

When the underlayer film composition contains the component (A) and the component (D), the content of the component (A) is preferably 1 to 30 parts by mass, and more preferably 1 to 10 parts by mass for 100 parts by mass of the component (D) (as complete hydrolysis condensate). If the content of the component (A) is below 1 part by mass, the adhesion to the resist (organic thin film) tends to decrease. On the other hand, if the content of the component (A) is exceeding 30 parts by mass, a footing of the resist pattern tends to increase.

When the composition underlayer film composition contains the component (B) and the component (D), the content of the component (B) is preferably 0.5 to 40 parts by mass, and more preferably 1 to 30 parts by mass for 100 parts by mass of the component (D) (as complete hydrolysis condensate). If the content of the component (B) is below 0.5 parts by mass, the adhesion to the resist (organic thin film) tends to decrease. On the other hand, if the content of the component (B) is exceeding 40 parts by mass, the footing of the resist pattern tends to increase.

The weight average molecular weight (Mw) of the component (D) is generally about 500 to 120,000, and preferably about 800 to 100,000. The weight average molecular weight (Mw) described in the present specification indicates a polystyrene-reduced weight average molecular weight measured using gel permeation chromatography (GPC).

(Polymer (E))

It is preferable that the underlayer film composition contains a polymer having a specific repeating unit (hereinafter referred to from time to time as "polymer (E)" or "component (E)") in addition to the component (A) and component (B). It is possible to have the underlayer film contain a component (E) by using the underlayer film composition containing the component (E).

The component (E) contains a repeating unit shown by the following formula (3) (hereinafter referred to from time to time as "unit (E-1)") and/or a repeating unit shown by the following formula (4) (hereinafter referred to from time to time as "unit (E-2)").

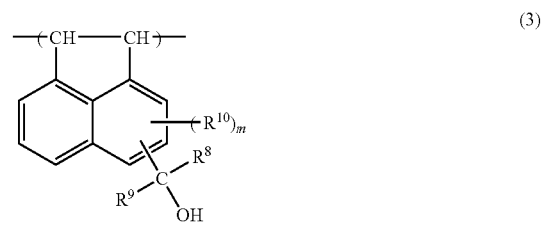

(3)

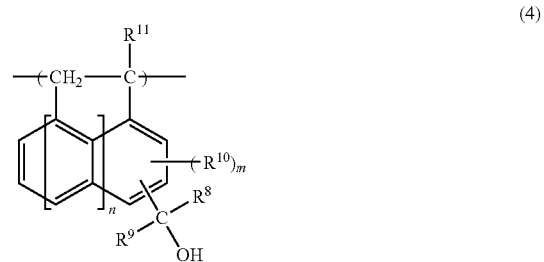

(4)

wherein, in the formulas (3) and (4), $R^8$ and $R^9$ represent a hydrogen atom, an alkyl group having 1 to 3 carbon atoms, or an aryl group, $R^{10}$ represents an alkyl group having 1 to 3 carbon atoms, a vinyl group, an allyl group, or an aryl group, $R^{11}$ represents a hydrogen atom or a methyl group, n represents 0 or 1, and m represents an integer of 0 to 2. As specific examples of the alkyl group having 1 to 3 carbon atoms represented by $R^8$ to $R^{10}$, a methyl group, an ethyl group, an n-propyl group, and an i-propyl group can be given. As specific examples of the aryl group represented by $R^8$ and $R^9$, a phenyl group, a tolyl group, a naphthyl group, and a biphenyl group can be given. In the formulas (3) and (4), $R^8$ and $R^9$ are preferably hydrogen atoms and n and m are preferably 0.

The weight average molecular weight (Mw) of the component (E) is 500 to 500,000, preferably 500 to 100,000, more preferably 800 to 50,000, and particularly preferably 800 to 10,000. If the weight average molecular weight of the component (E) is below 500, the component volatilizes during sintering of the film and a desired film thickness may not be obtained. If exceeding 500,000, on the other hand, solubility in the solvent may decrease.

The total amount of the units (E-1) and (E-2) contained in the polymer (E) is generally 10 to 90 mol %, and preferably 30 to 70 mol %. The total amount of the units (E-1) and (E-2) in the polymer (E) in the above range ensures improvement of etching resistance. If the content of the units (E-1) and (E-2) is below 10 mol %, adhesion to the resist (organic thin film) tends to decrease. If exceeding 90 mol %, on the other hand, the footing of the resist pattern tends to increase.

The polymer (E) may contain "other repeating units" other than the repeating unit (E-1) and repeating unit (E-2). As monomers used for forming such "other repeating units", 2-hydroxyethyl methacrylate, glycidyl methacrylate, N-methylacrylamide, and the like can be given. The "other repeating units" included in the polymer (E) may be one or may be two or more. The content of the "other repeating units" in the polymer (E) is preferably 30 to 90 mol %, and more preferably 50 to 70 mol %.

When the underlayer film composition contains the component (A) and the component (E), the content of the component (A) is preferably 1 to 30 parts by mass, and more preferably 1 to 10 parts by mass for 100 parts by mass of the component (E) (as complete hydrolysis condensate). If the content of the component (A) is below 1 part by mass, the adhesion to the resist (organic thin film) tends to decrease. On the other hand, if the content of the component (A) is exceeding 30 parts by mass, the footing of the resist pattern tends to increase.

When the underlayer film composition contains the component (B) and the component (E), the content of the component (B) is preferably 0.5 to 40 parts by mass, and more preferably 1 to 30 parts by mass for 100 parts by mass of the component (E) (as complete hydrolysis condensate). If the content of the component (B) is below 0.5 parts by mass, adhesion to the resist (organic thin film) tends to decrease. On the other hand, if the content of the component (B) is exceeding 40 parts by mass, the footing of the resist pattern tends to increase.

(Synthetic Method of Polymer (E))

The polymer (E) can be obtained by polymerizing a monomer shown by the following formula (3-1) and/or a monomer shown by the following formula (4-1).

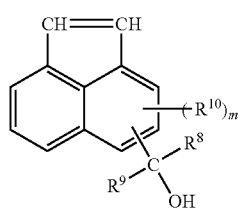

(3-1)

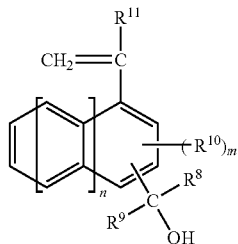

(4-1)

In the formulas (3-1) and (4-1), $R^8$, $R^9$, $R^{10}$, $R^{11}$, n, and m are the same as $R^8$, $R^9$, $R^{10}$, $R^{11}$, n and m in the formulas (3) and (4).

The polymer (E) can be prepared by, for example, causing polymerizable unsaturated monomers corresponding to the repeating units for forming a desired molecular composition to polymerize in a specified solvent in the presence of a radical polymerization initiator, a chain transfer agent, and the like. In order to realize a sufficient rate of polymerization, the radical polymerization initiator is preferably added at a sufficiently high concentration. If the proportion of the radical polymerization initiator to the amount of a chain transfer agent is too large, a radical-radical coupling reaction may occur and undesirable non-living radical polymer tends to be produced. A polymer containing a portion having uncontrolled polymer characteristics (e.g. molecular weight, molecular weight distribution, etc.) may be produced. Therefore, the molar ratio of the radical polymerization initiator to the chain transfer agent is preferably 1:1 to 0.005:1.

Although there are no limitations to the radical polymerization initiator, a thermal polymerization initiator, a redox polymerization initiator, and a photo-polymerization initiator can be given as examples. As specific examples of the radical polymerization initiator, initiators such as peroxides and azo compounds can be given. More specific examples of radical polymerization initiators include, t-butyl hydroperoxide, t-butyl perbenzoate, benzoyl peroxide, t-butylpivalate, 2,2'-azobis(2,4-dimethylvaleronitrile), 2,2'-azobisisobutyronitrile (AIBN), 1,1'-azobis(cyclohexanecarbonitrile), dimethyl 2,2'-azobisisobutyrate (MAM), and the like. As the chain transfer agent, pyrazole derivatives, alkyl thiols, and the like can be given.

As the method of polymerization, generally used batch polymerization, dripping polymerization, and the like can be given. For example, the polymer (A) may be obtained by dissolving the monomer shown by the formula (3-1) and the monomer shown by the formula (4-1) in an appropriate amount of an organic solvent and polymerizing the monomers in the presence of the radical polymerization initiator and the chain transfer agent. The organic solvent capable of dissolving the monomers, radical polymerization initiators, and chain transfer agents is generally used as the polymerization solvent. As specific examples of the organic solvent, alcohol solvents, ketone solvents, ether solvents, aprotic polar solvents, ester solvents, aromatic solvents, and linear or cyclic aliphatic solvents can be given. As alcohol solvents, 2-propanol, butanol, propylene glycol monomethyl ether, and the like can be given. As ketone solvents, methyl ethyl ketone, acetone, and the like can be given. Examples of the ether solvents include alkoxyalkyl ethers such as methoxymethyl ether, ethyl ether, tetrahydrofuran, and 1,4-dioxane. Examples of the aprotic polar solvents include dimethylformamide, dimethylsulfoxide, and the like. As ester solvents, alkyl acetates, such as ethyl acetate, and methyl acetate, and the like can be given. Examples of the aromatic solvents include alkyl aryl solvents such as toluene and xylene, halogenated aromatic solvents such as chlorobenzene, and the like. Examples of the aliphatic solvents include hexane, cyclohexane, and the like.

The polymerization temperature is generally 20 to 120° C., preferably 50 to 110° C., and more preferably 60 to 100° C. Although polymerization may also be conducted in a normal atmosphere, polymerization is preferably conducted in an inert gas atmosphere such as nitrogen and argon. The molecular weight of the polymer (E) can be adjusted by controlling the ratio of the monomers and the chain transfer agent. The polymerization time is generally 0.5 to 144 hours, preferably 1 to 72 hours, and more preferably 2 to 24 hours.

(Polymer (F))

It is preferable that the underlayer film composition contains a polymer having a specific repeating unit (hereinafter referred to from time to time as "polymer (F)" or "component (F)") in addition to the component (A) and the component (B). It is possible to have the underlayer film contain a component (F) by using the underlayer film composition containing the component (F).

The component (F) contains a repeating unit shown by the following formula (5) (hereinafter referred to from time to time as "unit (F-1)").

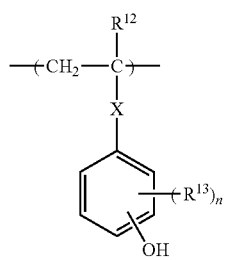

(5)

wherein, in the formula (5), $R^{12}$ represents a hydrogen atom or a methyl group, $R^{13}$ represents an alkyl group having 1 to 3 carbon atoms, a vinyl group, an allyl group, or an aryl group, X represents a single bond, —C(=O)—O—, or —C(=O)—NH—, and n represents an integer of 0 to 4.

As specific examples of the alkyl group having 1 to 3 carbon atoms represented by $R^{13}$, a methyl group, an ethyl group, an n-propyl group, and an i-propyl group can be given. As specific examples of the aryl group represented by $R^{13}$, a phenyl group, a tolyl group, a naphthyl group, and a biphenyl group can be given. $R^{12}$ in the formula (5) is preferably a hydrogen atom and n is preferably 0.

The weight average molecular weight (Mw) of the component (F) is 500 to 500,000, preferably 500 to 100,000, more preferably 800 to 50,000, and particularly preferably 800 to 20,000. If the weight average molecular weight of the component (F) is below 500, the component volatilizes during sintering of the film and a desired film thickness may not be obtained. If exceeding 500,000, solubility of the component (F) in the solvent may decrease.

The amount of the unit (F-1) contained in the polymer (F) is preferably 50 mol % or more, more preferably 60 mol % or more, and particularly preferably 70 mol % or more.

When the underlayer film composition contains the component (A) and the component (F), the content of the component (A) is preferably 1 to 30 parts by mass, and more preferably 1 to 10 parts by mass for 100 parts by mass of the component (F) (as complete hydrolysis condensate). If the content of the component (A) is below 1 part by mass, the adhesion to the resist (organic thin film) tends to decrease. On the other hand, if the content of the component (A) is exceeding 30 parts by mass, the footing of the resist pattern tends to increase.

When the underlayer film composition contains the component (B) and the component (F), the content of the component (B) is preferably 0.5 to 40 parts by mass, and more preferably 1 to 30 parts by mass for 100 parts by mass of the component (F) (as complete hydrolysis condensate). If the content of the component (B) is below 0.5 parts by mass, the adhesion to the resist (organic thin film) tends to decrease. On the other hand, if the content of the component (B) is exceeding 40 parts by mass, the footing of the resist pattern tends to increase.

(Synthetic Method of Polymer (F))

The polymer (F) can be obtained by polymerizing a monomer shown by the following formula (5-2) and/or a monomer shown by the following formula (5-3). When polymerizing the monomer shown by the following formula (5-2), hydrolysis by an acid or a base is required after the polymerization according to the method described in JP-A-2004-54209 or JP-A-2006-131869.

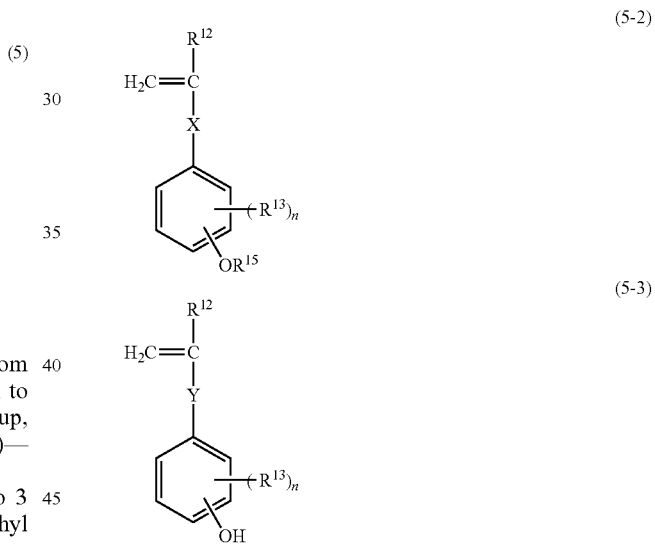

wherein, in the formulas (5-2) and (5-3), $R^{12}$, $R^{13}$, and n are the same as the $R^{12}$, $R^{13}$, and n in the formula (5). $R^{15}$ is a monovalent organic group. As specific examples, a 1-ethoxyethyl group, an acetyl group, and a t-butyl group can be given. Y is —C(=O)—O— or —C(=O)—NH—.

The polymer (F) may be prepared by, for example, causing polymerizable unsaturated monomers corresponding to the repeating units for forming a desired molecular composition to polymerize in a specified solvent in the presence of a radical polymerization initiator, the chain transfer agent, and the like. In order to realize a sufficient rate of polymerization, the radical polymerization initiator is preferably added at a sufficiently high concentration. If the proportion of the radical polymerization initiator to the amount of the chain transfer agent is too large, a radical-radical coupling reaction may occur and undesirable non-living radical polymers tend to be produced. A polymer containing a portion having uncontrolled polymer characteristics (e.g. molecular weight, molecular weight distribution, etc.) may be produced. Therefore, the molar ratio of the radical polymerization initiator to the chain transfer agent is preferably 1:1 to 0.005:1.

Although there are no limitations to the radical polymerization initiator, a thermal polymerization initiator, a redox polymerization initiator, and a photo-polymerization initiator can be given as examples. As specific examples of the radical polymerization initiator, initiators such as peroxides and azo compounds can be given. More specific examples of the radical polymerization initiators include, t-butylhydroperoxide, t-butylperbenzoate, t-butylpivalate, benzoylperoxide, 2,2'-azobis(2,4-dimethylvaleronitrile), 2,2'-azobisisobutyronitrile (AIBN), 1,1'-azobis(cyclohexanecarbonitrile), dimethyl 2,2'-azobisisobutyrate (MAIB), and the like. As the chain transfer agent, pyrazole derivatives, alkyl thiols, and the like can be given.

As the method of polymerization, generally used batch polymerization, dripping polymerization, and the like can be given. For example, the polymer (F) may be obtained by dissolving the monomer shown by the formula (5-2) and the monomer shown by the formula (5-3) in an appropriate amount of an organic solvent and polymerizing the monomers in the presence of the radical polymerization initiator and the chain transfer agent. The organic solvent capable of dissolving the monomers, radical polymerization initiators, and chain transfer agents is generally used as the polymerization solvent. As specific examples of the organic solvent, alcohols, ketones, ethers, aprotic polar solvents, esters, aromatic solvents, and linear or cyclic aliphatic solvents can be given. As alcohol solvents, 2-propanol, butanol, propylene glycol monomethyl ether, and the like can be given. As ketone solvents, methyl ethyl ketone, acetone, and the like can be given. Examples of the ether solvents include alkoxyalkyl ethers such as methoxymethyl ether, ethyl ether, tetrahydrofuran, and 1,4-dioxane. Examples of the aprotic polar solvents include dimethylformamide, dimethylsulfoxide, and the like. As ester solvents, alkyl acetates such as ethyl acetate, methyl acetate, and the like can be given. Examples of the aromatic solvents include alkyl aryl solvent such as toluene and xylene, halogenated aromatic solvents such as chlorobenzene, and the like. Examples of the aliphatic solvents include hexane, cyclohexane, and the like.

The polymerization temperature is generally 20 to 120° C., preferably 50 to 110° C., and more preferably 60 to 100° C. Although polymerization may also be conducted in a normal atmosphere, polymerization is preferably conducted in an inert gas atmosphere such as nitrogen and argon. The molecular weight of the polymer (F) can be adjusted by controlling the ratio of the monomers and the chain transfer agent. The polymerization time is generally 0.5 to 144 hours, preferably 1 to 72 hours, and more preferably 2 to 24 hours.

After the copolymerization, the resulting copolymer is hydrolyzed, whereby the side chains of the monomer shown by the formula (5-2) is completely hydrolyzed into a repeating unit having a phenolic hydroxyl group on the side chain. The conditions and method of hydrolyzing the side chains of the monomer of the formula (5-2) are described below.

The hydrolysis reaction is carried out using an acid catalyst or a base catalyst. As the acid catalyst used for the hydrolysis reaction, hydrochloric acid, sulfuric acid, and organic acids such as p-toluenesulfonic acid and its hydrate, methanesulfonic acid, trifluoromethanesulfonic acid, malonic acid, oxalic acid, 1,1,1-trifluoroacetic acid, acetic acid, and pyridinium p-toluenesulfonate can be given. As the base catalyst, inorganic bases such as potassium hydroxide, sodium hydroxide, sodium carbonate, and potassium carbonate; organic bases such as triethylamine, N-methyl-2-pyrrolidone, piperidine, and tetramethylammonium hydroxide; and the like can be given.

As a suitable organic solvent used for the hydrolysis reaction, ketones such as acetone, methyl ethyl ketone, and methyl amyl ketone; ethers such as diethyl ether and tetrahydrofuran (THF); alcohols such as methanol, ethanol, and propanol; aliphatic hydrocarbons such as hexane, heptane, and octane; aromatic hydrocarbons such as benzene, toluene, and xylene; alkyl halides such as chloroform, bromoform, methylene chloride, methylene bromide, and carbon tetrachloride; esters such as ethyl acetate, butyl acetate, ethyl lactate, propylene glycol monomethyl ether, propylene glycol monomethyl ether acetate, and cellosolves; aprotic polar solvents such as dimethylformamide, dimethylsulfoxide, and hexamethyl phosphoroamide; and the like can be given. Among these, particularly suitable solvents are acetone, methyl amyl ketone, methyl ethyl ketone, tetrahydrofuran, methanol, ethanol, propanol, ethyl acetate, butyl acetate, ethyl lactate, propylene glycol monomethyl ether, propylene glycol monomethyl ether acetate, and the like.

Hydrolysis of the side chain of the monomer shown by the above formula (5-2) is carried out using a solution of a monomer with a concentration of generally 1 to 50 mass %, preferably 3 to 40 mass %, and more preferably 5 to 30 mass %, at a reaction temperature of generally −20 to 100° C., preferably 0 to 80° C., and more preferably 5 to 80° C. for a reaction time, which may differ according to the temperature, but generally of 10 minutes to 20 hours, preferably 30 minutes to 10 hours, and more preferably 1 to 6 hours. As the hydrolysis method, a method of dissolving the copolymer in the organic solvent, adding an acid catalyst or a base catalyst, and stirring the mixture can be given, for example.

(Organic Solvent)

The underlayer film composition can be prepared by dissolving the above component (A) or component (B), and optionally used component (D), component (E), or component (F) in an appropriate organic solvent. The total solid concentration of the underlayer film composition is preferably 0.5 to 20 mass % and is appropriately adjusted according to purpose of use. If the total solid concentration of the underlayer film composition is in the range of 0.5 to 20 mass %, the resulting underlayer film has an appropriate thickness and has increased storage stability.

Examples of the organic solvents used for dissolving the component (D) include aliphatic hydrocarbon solvents such as n-pentane, i-pentane, n-hexane, i-hexane, n-heptane, i-heptane, 2,2,4-trimethylpentane, n-octane, i-octane, cyclohexane, and methyl cyclohexane; aromatic hydrocarbon solvents such as benzene, toluene, xylene, ethylbenzene, trimethylbenzene, methylethylbenzene, n-propylbenzene, i-propylbenzene, diethylbenzene, i-butylbenzene, triethylbenzene, di-i-propylbenzene, n-amylnaphthalene, and trimethylbenzene; monoalcohol solvents such as methanol, ethanol, n-propanol, i-propanol, n-butanol, i-butanol, sec-butanol, t-butanol, n-pentanol, i-pentanol, 2-methylbutanol, sec-pentanol, t-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethylheptanol-4, n-decanol, sec-undecyl alcohol, trimethylnonyl alcohol, sec-tetradecyl alcohol, sec-heptadecyl alcohol, phenol, cyclohexanol, methylcyclohexanol, 3,3,5-trimethylcyclohexanol, benzyl alcohol, phenyl methyl carbinol, diacetone alcohol, and cresol; polyhydric alcohol solvents such as ethylene glycol, propylene glycol, 1,3-butylene glycol, pentanediol-2,4,2-methylpentanediol-2,4, hexanediol-2,5, heptanediol-2,4,2-ethylhexanediol-1,3, diethylene glycol, dipropylene glycol, triethylene glycol, tripropylene glycol, and glycerol; ketone solvents such as acetone, methyl ethyl ketone, methyl n-propyl ketone, methyl n-butyl ketone, diethyl ketone, methyl i-butyl ketone, methyl n-pentyl ketone, ethyl n-butyl ketone, methyl n-hexyl ketone, di-i-butyl ketone, trimethyl nonanon, cyclohexanone, methylcyclohexanone, 2,4-pentanedione, acetonyl acetone, diacetone alcohol, acetophenone, and fenchone; ether solvents such as ethyl ether, i-propyl ether, n-butyl ether, n-hexyl ether, 2-ethylhexyl ether, ethylene oxide, 1,2-propylene oxide, dioxolane, 4-methyldioxolane, dioxane, dimethyl dioxane, ethylene glycol monomethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-2-ethyl butyl ether, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tetrahydrofuran, and 2-methyltetrahydrofuran;

ester solvents such as diethyl carbonate, methyl acetate, ethyl acetate, γ-butyrolactone, γ-valerolactone, n-propyl acetate, i-propyl acetate, n-butyl acetate, i-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetoate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxy triglycol acetate, ethyl propionate, n-butyl propionate, i-amyl propionate, diethyl oxalate, di-n-butyl oxalate, methyl lactate, ethyl lactate, n-butyl lactate, n-amyl lactate, diethyl malonate, dimethyl phthalate, and diethyl phthalate; nitrogen-containing solvents such as N-methylformamide, N,N-dimethylformamide, N,N-diethylformamide, acetamide, N-methylacetamide, N,N-dimethylacetamide, N-methylpropionamide, and N-methylpyrrolidone; and sulfur-containing solvents such as dimethyl sulfide, diethyl sulfide, thiophene, tetrahydrothiophene, dimethyl sulfoxide, sulfolane, and 1,3-propane sultone.

Among these, the organic solvent shown by the following formula (19) is preferably used as the solvent for the component (D).

$$R^{16}O(R^{18}O)_eR^{17} \quad (19)$$

wherein, in the formula (19), $R^{16}$ and $R^{17}$ individually represent a monovalent organic group, $R^{18}$ represents an alkylene group having 2 to 4 carbon atoms, and e represents an integer of 1 to 2. Examples of the monovalent organic group include a hydrogen atom, an alkyl group having 1 to 4 carbon atoms, $CH_3CO-$, and the like.

Examples of the organic solvent shown by the above formula (19) include propylene glycol monomethyl ether, propylene glycol monoethyl ether, propylene glycol monopropyl ether, propylene glycol monobutyl ether, propylene glycol dimethyl ether, propylene glycol diethyl ether, propylene glycol dipropyl ether, propylene glycol dibutyl ether, dipropylene glycol monomethyl ether, dipropylene glycol monoethyl ether, dipropylene glycol monopropyl ether, dipropylene glycol monobutyl ether, dipropylene glycol dimethyl ether, dipropylene glycol diethyl ether, dipropylene glycol dipropyl ether, dipropylene glycol dibutyl ether, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, dipropylene glycol monopropyl ether acetate, dipropylene glycol monobutyl ether acetate, propylene glycol diacetate, dipropylene glycol diacetate, and propylene glycol. Among these, propylene glycol monomethyl ether, propylene glycol monoethyl ether, propylene glycol monopropyl ether, propylene glycol monobutyl ether, propylene glycol dimethyl ether, propylene glycol diethyl ether, propylene glycol monomethyl ether acetate, propylene glycol monoethyl ether acetate, and propylene glycol monopropyl ether acetate are preferable due to excellent storage stability.

As the solvent for the component (E) and the component (F), monoalcohol solvents such as methanol, ethanol, n-propanol, i-propanol, n-butanol, 1-butanol, sec-butanol, t-butanol, n-pentanol, i-pentanol, 2-methylbutanol, sec-pentanol, t-pentanol, 3-methoxybutanol, n-hexanol, 2-methylpentanol, sec-hexanol, 2-ethylbutanol, sec-heptanol, heptanol-3, n-octanol, and 2-ethylhexanol;

polyhydric alcohol solvents such as ethylene glycol, propylene glycol, 1,3-butylene glycol, pentanediol-2,4,2-methylpentanediol-2,4, hexanediol-2,5, heptanediol-2,4,2-ethylhexanediol-1,3, diethylene glycol, dipropylene glycol, triethylene glycol, tripropylene glycol, and glycerol; ketone solvents such as acetone, methyl ethyl ketone, methyl n-propyl ketone, methyl n-butyl ketone, diethyl ketone, methyl i-butyl ketone, methyl n-pentyl ketone, ethyl n-butyl ketone, methyl n-hexyl ketone, di-i-butyl ketone, trimethyl nonanon, cyclohexanone, and methylcyclohexanone; ether solvents such as dioxane, dimethyl dioxane, ethylene glycol monomethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-n-ethyl butyl ether, ethylene glycol dibutyl ether, diethylene glycol monomethyl ether, ethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tetrahydrofuran, and 2-methyltetrahydrofuran;

ester solvents such as methyl acetate, ethyl acetate, γ-butyrolactone, γ-valerolactone, n-propyl acetate, i-propyl acetate, n-butyl acetate, i-butyl acetate, sec-butyl acetate, n-pentyl acetate, sec-pentyl acetate, 3-methoxy butyl acetate, pentyl methyl-acetate, 2-ethyl butyl acetate, 2-ethylhexyl acetate, benzyl acetate, cyclohexyl acetate, methyl cyclohexyl acetate, n-nonyl acetate, methyl acetoacetoate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxy triglycol acetate, ethyl propionate, n-butyl propionate, i-amyl propionate, diethyl oxalate, di-n-butyl oxalate, methyl lactate, ethyl lactate, n-butyl lactate, n-amyl lactate, diethyl malonate, dimethyl phthalate, and diethyl phthalate; and nitrogen-containing solvents such as N-methylformamide, N,N-dimethylformamide, N,N-diethylformamide, acetamide, N-methylacetamide, N,N-dimethylacetamide, N-methylpropionamide, and N-methylpyrrolidone are preferable.

(Other Components)

Components such as β-diketone, colloidal silica, colloidal alumina, an organic polymer, a crosslinking agent, a binder resin, a surfactant, a preservative, a defoamer, an adhesion adjuvant, and the like may be optionally added to the underlayer film composition as needed.

For example, when the underlayer film composition contains the component (D), a β-diketone may be added. As examples, acetylacetone, 2,4-hexanedione, 2,4-heptanedione, 3,5-heptanedione, 2,4-octanedione, 3,5-octanedione, 2,4-nonanedione, 3,5-nonanedione, 5-methyl-2,4-hexanedione, 2,2,6,6-tetramethyl 3,5-heptanedione, 1,1,1,5,5,5-hexafluoro-2,4-heptanedione, and the like can be given. These β-diketones can be used individually or in combination of two or more.

The content of β-diketones in the underlayer film composition is preferably 1 to 50 mass %, and more preferably 3 to 30 mass % for 100 mass % of the organic solvent. The addition of β-diketones in an amount of this range improves storage stability and prevents a decrease in the properties of the composition such as capability for forming films with a uniform thickness.

For example, when the underlayer film composition contains the component (D), colloidal silica may be added. Colloidal silica is, for example, a dispersion of high purity silicic anhydride in hydrophilic organic solvent, in which the particles have an average diameter generally of 5 to 30 μm, and preferably 10 to 20 μm and the solid concentration is generally about 10 to 40 mass %. As specific examples of colloidal silica, methanol silica sol, isopropanol silica sol (manufactured by Nissan Chemical Industries, Ltd.); "Oscar" (manufactured by Catalysts & Chemicals Ind. Co., Ltd.), and the like can be given.

As specific examples of colloidal alumina, "Alumina Sol 520", "Alumina Sol 100", and "Alumina Sol 200" (manufactured by Nissan Chemical Industries, Ltd.); "Alumina Clear Sol", "Alumina Sol 10", and "Alumina Sol 132" (manufactured by Kawasaki Fine Chemicals Co., Ltd.), and the like can be given.

For example, when the underlayer film composition contains the component (D), an organic polymer may be added. As examples of the organic polymer, a compound having a polyalkylene oxide structure, a compound having a sugar chain structure, a vinyl amide polymer, a (meth)acrylate polymer, an aromatic vinyl compound polymer, a dendrimer, a polyimide, a polyamic acid, a polyarylene, a polyamide, a polyquinoxaline, a polyoxadiazole, a fluoropolymer, and the like can be given.

The crosslinking agent is a component to accelerate the reactivity of the polymer (E) containing the unit (E-1) and/or unit (E-2) or the polymer (F) with a resist (organic thin film) when the composition for underlayer film contains these polymers. The crosslinking agent is a component having a function of suppressing generation of cracks after application of the underlayer film composition.

As the acrosslinking agent, polynuclear phenols and various commercially-available curing agents may be used. Specific examples of the polynuclear phenols include binuclear phenols such as 4,4'-biphenyldiol, 4,4'-methylenebisphenol, 4,4'-ethylidenebisphenol, and bisphenol A; trinuclear phenols such as 4,4',4''-methylidenetrisphenol, and 4,4'-[1-{4-(1-[4-hydroxyphenyl]-1-methylethyl)phenyl}ethylidene]bisphenol; and polyphenols such as novolak. Of these, 4,4'-[1-{4-(1-[4-hydroxyphenyl]-1-methylethyl)phenyl}ethylidene]bisphenol, novolak, and the like are preferable. These polynuclear phenols can be used individually or in combination of two or more.

Specific examples of the curing agent include diisocyanates such as 2,3-tolylenediisocyanate, 2,4-tolylenediisocyanate, 3,4-tolylenediisocyanate, 3,5-tolylenediisocyanate, 4,4'-diphenylmethanediisocyanate, hexamethylenediisocyanate, and 1,4-cyclohexanediisocyanate; epoxy compounds available under the trade names of Epicoat 812, Epicoat 815, Epicoat 826, Epicoat 828, Epicoat 834, Epicoat 836, Epicoat 871, Epicoat 1001, Epicoat 1004, Epicoat 1007, Epicoat 1009, and Epicoat 1031 (manufactured by Yuka-Shell Epoxy Co., Ltd.), Araldite 6600, Araldite 6700, Araldite 6800, Araldite 502, Araldite 6071, Araldite 6084, Araldite 6097, and Araldite 6099 (manufactured by Ciba Geigy Corp.), DER 331, DER 332, DER 333, DER 661, DER 644, and DER 667 (manufactured by Dow Chemical Company); melamine curing agents such as Cymel 300, Cymel 301, Cymel 303, Cymel 350, Cymel 370, Cymel 771, Cymel 325, Cymel 327, Cymel 703, Cymel 712, Cymel 701, Cymel 272, Cymel 202, Mycoat 506, and Mycoat 508 (manufactured by Mitsui-Cyanamid Ltd.); benzoguanamine curing agents such as Cymel 1123, Cymel 1123-10, Cymel 1128, Mycoat 102, Mycoat 105, Mycoat 106, and Mycoat 130 (manufactured by Mitsui-Cyanamid Ltd.); and glycoluril curing agents such as Cymel 1170 and Cymel 1172 (manufactured by Mitsui-Cyanamid Ltd.), and NIKALAC N-2702 (manufactured by Sanwa Chemical Co., Ltd.). Among these, the melamine curing agents, the glycoluril curing agents, and the like are preferable. These curing agents can be used individually or in combination of two or more. The polynuclear phenols and the curing agents may be used in combination as the acrosslinking agent.

The amount of the crosslinking agent is preferably 50 mass % or less, and more preferably 30 mass % or less for 100 mass % of the solid component contained in the underlayer film composition. If the content of the crosslinking agent is exceeding 50 parts by mass, the footing of the resist pattern tends to increase.

A binder resin may be added when the underlayer film composition contains the polymer (E), which contains the unit (E-1) and/or unit (E-2), and polymer (F). As the binder resin, various thermoplastic resins and thermoset resins may be used. Specific examples of the thermoplastic resin include α-olefin polymers such as polyethylene, polypropylene, poly-1-butene, poly-1-pentene, poly-1-hexene, poly-1-heptene, poly-1-octene, poly-1-decene, poly-1-dodecene, poly-1-tetradecene, poly-1-hexadecene, poly-1-octadecene, and polyvinyl cycloalkane; non-conjugated diene polymers such as poly-1,4-pentadiene, poly-1,4-hexadiene, and poly-1,5-hexadiene; α,β-unsaturated aldehyde polymers; α,β-unsaturated ketone polymers such as poly(methyl vinyl ketone), poly(aromatic vinyl ketone), and poly(cyclic vinyl ketone); α,β-unsaturated carboxylic acid polymers or α,β-unsaturated carboxylic acid derivative polymers such as (meth)acrylic acid, α-chloroacrylic acid, (meth)acrylic acid salt, (meth)acrylate, and halogenated (meth)acrylic acid; α,β-unsaturated carboxylic acid anhydride polymers such as a copolymer of poly(meth) acrylic acid anhydride and maleic acid unhydride; unsaturated polybasic calboxylate polymers such as methylene malonic acid diester and itaconic acid diester;

polyimines; polyethers such as polyphenyleneoxide, poly-1,3-dioxolan, polyoxolan, polytetrahydrofuran, and polytetrahydropyrane; polysulfides; polysulfonamides; polypeptides; polyamides such as nylon 66 and nylons 1 to 12; polyesters such as aliphatic polyesters, aromatic polyesters, alicyclic polyesters, and polycarbonate esters; polyureas; polysulfones; polyazines; polyamines; polyaromatic ketones; polyimides; polybenzoimidazoles; polybenzooxazols; polybenzothiazoles; polyaminotriazoles; polyoxadiazoles; polypyrazoles; polytetrazoles; polyquinoxalines; polytriazines; polybenzoxadinones; polyquinolines; and polyanthrazolines.

The thermoset resin is a component which is cured by heating and becomes insoluble in a solvent. The thermoset resin is suitably used as a binder resin. As specific examples of the thermoset resin, heat-curable acrylic resins, phenol resins, urea resins, melamine resins, amino resins, aromatic hydrocarbon resins, epoxy resins, alkyd resins, and the like can be given. Of these, urea resins, melamine resins, aromatic hydrocarbon resins, and the like are preferable. These binder resins can be used individually or in combination of two or more.

The amount of the binder resin added is preferably 20 mass % or less, and more preferably 10 mass % or less for 100 mass % of the solid component. Tithe amount of the binder resin is exceeding 20 mass %, the reactivity with the resist (organic thin film) tends to decrease.

The surfactant improves applicability, striation, developability, and the like. As specific examples of the surfactant, a nonionic surfactant, an anionic surfactant, a cationic surfactant, an amphoteric surfactant, a silicon-containing surfactant, a polyalkylene oxide surfactant, a fluorine-containing surfactant, an acrylic surfactant, and the like can be given.

As further specific examples of the surfactant, polyoxyethylene alkyl ethers such as polyoxyethylene lauryl ether, polyoxyethylene stearyl ether, and polyoxyethylene oleyl ether; polyoxyethylene alkyl phenyl ethers such as polyoxyethylene n-octyl phenyl ether and polyoxyethylene n-nonyl phenyl ether; polyethylene glycol diesters such as polyethylene glycol dilaurate and polyethylene glycol distearate; sorbitan fatty acid esters; fatty acid-modified polyesters; tertiary amine-modified polyurethanes; polyethylene imines; and commercially available products such as KP (manufactured by Shin-Etsu Chemical Co., Ltd.), POLYFLOW (manufactured by Kyoeisha Chemical Co., Ltd.), FTOP (manufactured by Tohkem Products Corporation), MEGAFAC (manufactured by Dainippon Ink and Chemicals, Inc.), Fluorad (manufactured by Sumitomo 3M Ltd.), Asahi Guard and Surflon (manufactured by Asahi Glass Co., Ltd.), Disperbyk (manufactured by Bigchemie Japan, Inc.), Solsperse (manufactured by Senega Co.), and the like can be given. These surfactants can be used individually or in combination of two or more.

The amount of the surfactant used is preferably 15 mass % or less, and more preferably 10 mass % or less for 100 mass % of the solid component contained in the underlayer film composition.

The underlayer film composition may contain water. The content of water in the under layer film composition is preferably 1 to 15 mass %. If the water content is below 1 mass %, a residue tends to remain on the surface when developing a resist (self-organized film) made from the underlayer film composition stored for a long time. On the other hand, if the water content is exceeding 15 mass %, applicability of the underlayer film composition tends to decrease.

The total amount of sodium and iron contained in the underlayer film composition is preferably 20 ppb or less, and more preferably 15 ppb or less. When the total amount of sodium and iron is 20 ppb or less, resolution of the resist (self-organized film) is improved. Since sodium and iron originate from the raw materials used, it is preferable to purify the raw materials by distillation and the like.

2. Second Step:

The second step is a step of irradiating the underlayer film with radiation rays through a mask with a predetermined pattern to obtain a portion having been selectively exposed through the predetermined pattern. Since the component (A) or the component (B) is contained in the underlayer film, an acid or a base is electively generated according to the pattern in the underlayer film by irradiation in a predetermined pattern, whereby an exposed underlayer film can be formed.

The type of radiation ray used for exposure of the underlayer film may be appropriately selected according to the type of the component (A) or the component (B). As specific radiation rays, deep ultraviolet rays such as an $F_2$ excimer laser (wavelength: 157 nm), an ArF excimer laser (wavelength: 193 nm), and a KrF excimer laser (wavelength: 248 nm), extreme ultraviolet radiation (ET TV), X-rays such as synchrotron radiation rays, and charged particle rays such as electron beams (EB) can be given. Irradiation conditions such as the exposure dose of irradiation are appropriately determined according to the kind of the underlayer film composition, kind of additives, and the like. EB, X rays, and EUV can be preferably used in the pattern forming method of the present invention.

3. Third Step:

The third step is a step of forming an organic thin film (C) on the underlayer to chemically bond the exposed areas of the underlayer film to the organic thin film formed on the exposed areas of the underlayer film.

(Organic Thin Film (C))

As a specific example of the organic thin film, a film used for immobilizing molecules on a solid surface can be given. Such an organic thin film may be prepared by the "self-organization method" which can form highly oriented, high density molecular layers. The self-organization method may control environmental and geometrical arrangement of molecules in an angstrom order.

The organic thin film prepared by the self-organization method (hereinafter referred to from time to time as "self-organized film") is one of the major methods of immobilizing organic molecules. This is a desirable method due to its simplicity. In addition, since the self-organized film has high heat stability due to chemical bonds that are present between molecules and a substrate (Si substrate, resist underlayer film, etc.), the self-organization method is an important technology for preparing a molecular device of an angstrom order. In addition, since such a self-organized film is basically a membrane formed by a self-set process, it is possible to spontaneously form detailed patterns. Therefore, if a self-organized film is used as a resist, it is possible to easily form micro patterns which are difficult to form by using the existing lithography.

The organic thin film consists of bonding functional groups, which are reactive with elements making up the surface of the underlayer film, and other linear molecules. The organic thin film contains molecules showing an extremely high orientation due to the interaction of the linear molecules. That is, the organic thin film is a uniform film in a molecular level in which molecules are oriented. The bonding functional groups of the organic thin film are generally protected by an acid-dissociable group or a base-dissociable group.

An acid or a base is generated in the underlayer film in a predetermined pattern by irradiation through a mask having a predetermined pattern. The organic thin film is deprotected by the generated acid or base, and chemically bonded by selectively reacting the patterned area of the underlayer film (exposed underlayer film portion) and the organic thin film. In this manner, micro patterns can be formed.

As preferable examples of the compounds for forming the organic thin film possessing the above-described characteristics, oligothiophene derivatives may be given. Oligothiophene derivatives are compounds having an organic group reactive with the underlayer film. The organic group reactive with the underlayer film is preferably protected by an acid-dissociable group or a base-dissociable group.

As preferable examples of the oligothiophene derivatives, compounds shown by the following formula (20) can be given.

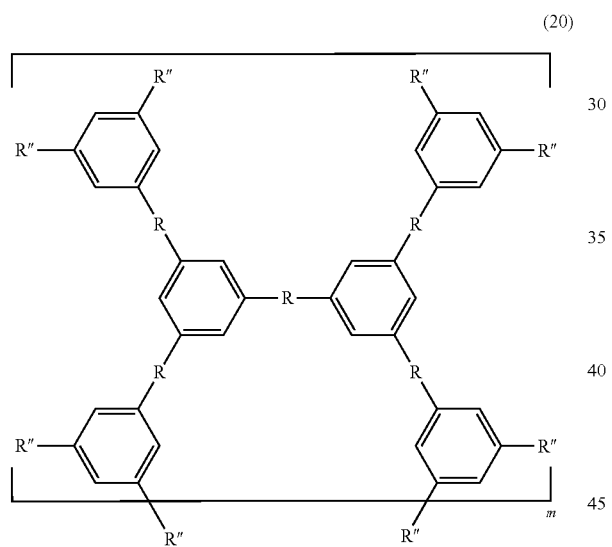

(20)

R in the formula (20) represents an oligothiophene which may have a substituent, R' individually represents an organic group protected by an acid-dissociable group or a base-dissociable group which is reactive with silanol terminals of the underlayer film, R" represents a monovalent organic group such as an alkyl group or a phenyl group, and m represents an integer of 1 or more. As preferable examples of the R in the formula (20), oligothiophenes shown by the following formulas (21) to (40) can be given. In the formulas (21) to (40), n is preferably 1.

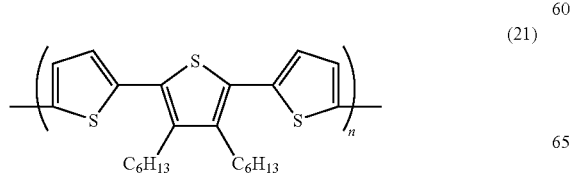

(21)

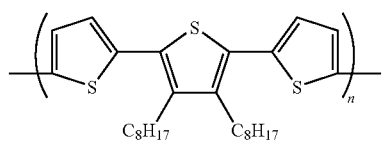

(22)

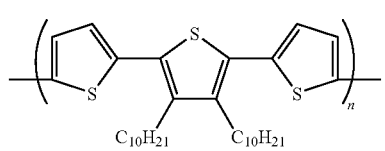

(23)

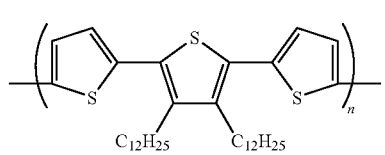

(24)

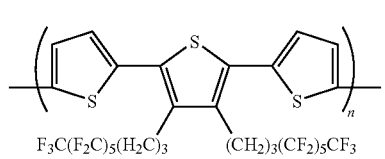

(25)

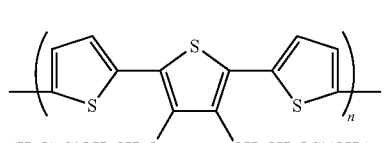

(26)

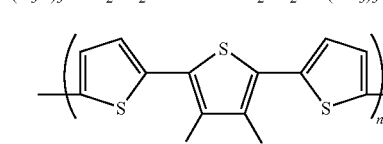

(27)

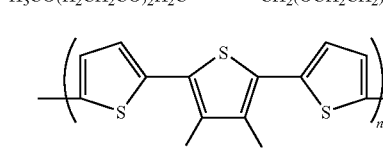

(28)

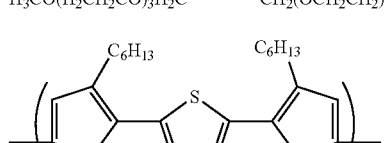

(29)

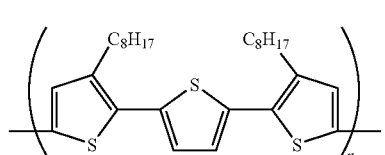

(30)

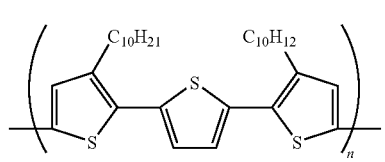

(31)

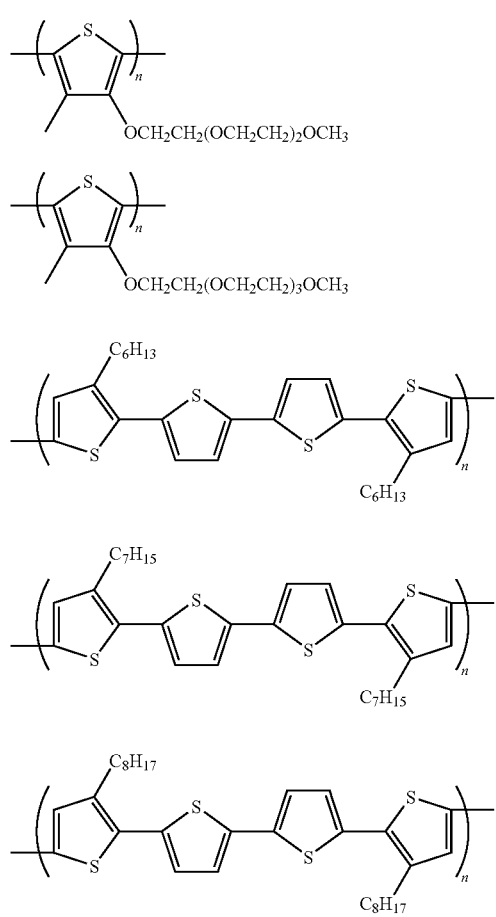
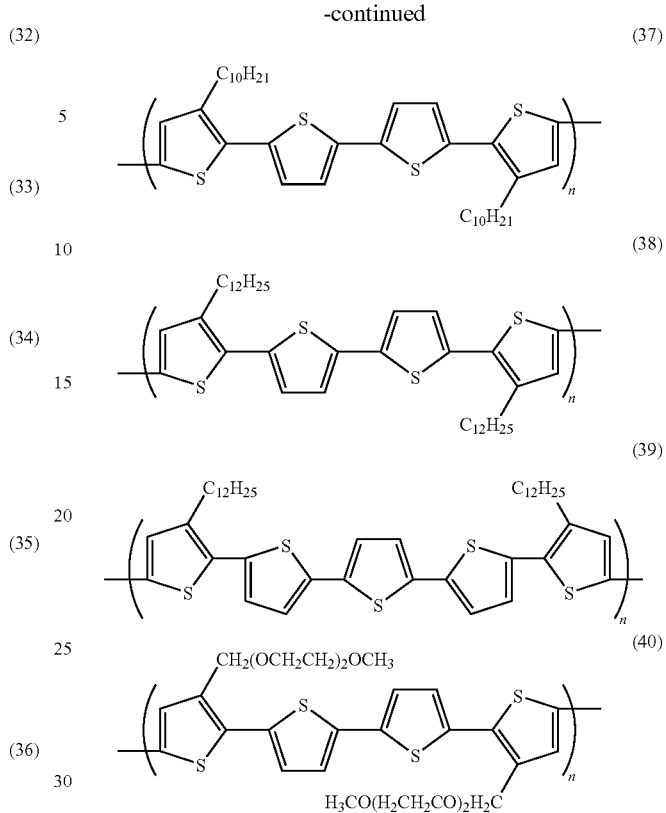
On the other hand, as preferable examples of the oligothiophene derivatives other than those shown by the formula (20), compounds shown by the following formula (41) and (42) can be given.
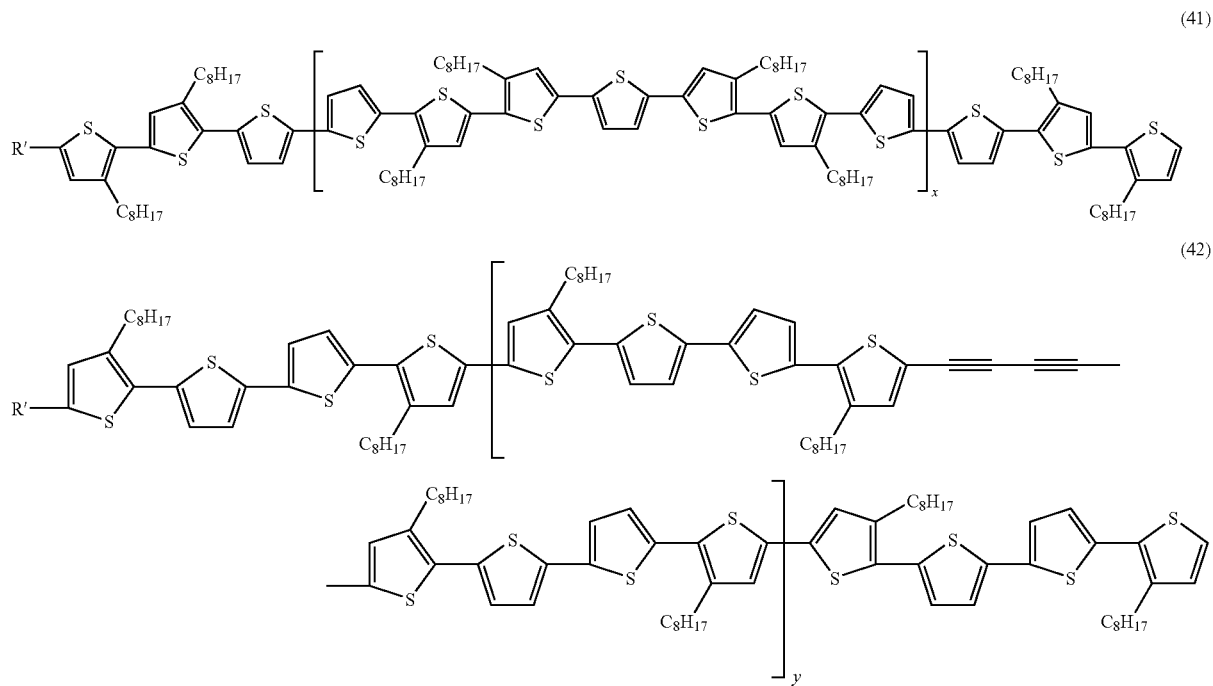

In the formula (41), x represents an integer of 1 or more. In the formula (42), y represents an integer of 1 or more. In the formulas (41) and (42), R' represents an organic group protected by an acid-dissociable group or a base-dissociable group. When the underlayer film has a silanol terminal, R' which is an organic group protected by an acid-dissociable group or a base-dissociable group in the formulas (41) and (42) is a group reactive with the silanol terminal.

The oligothiophene derivatives shown by the above formulas (41) or (42), excluding the portion shown by R', can be synthesized by a method described in the following documents, for example.

J. Org. Chem., 1998, 63, p. 8632
Bull. Chem. Soc. Jpn., 2001, 74, p. 979
Org. Lett., 2002, 4, p. 2533
J. Am. Chem. Soc., 2003, 125, p. 5286

R' in the formulas (20), (41) and (42) represents an organic group protected by an acid-dissociable group or a base-dissociable group, as mentioned above. When R' is an organic group protected by an acid-dissociable group, a group shown by the following formula (7) can be given as a specific example of the acid-dissociable group.

$$-Si(OR^{17})_3 \qquad (7)$$

wherein, in the formula (7), $R^{17}$'s may be the same or different and each independently represents an alkyl group having 1 to 5 carbon atoms, an aryl group having 6 to 14 carbon atoms, an allyl group, a glycidyl group, or a hydrogen atom. $R^{17}$ is preferably an alkyl group or a phenyl group. As examples of the alkyl group, a methyl group, an ethyl group, a propyl group, a butyl group, and the like can be given. These alkyl groups may be linear or branched, and the hydrogen atoms may be replaced by fluorine atoms and the like.

The organic thin film may be formed by applying the organic thin film forming composition containing an oligothiophene derivative and a solvent, which is one of the embodiments of the present invention. After applying the organic thin film forming composition in the form of a film, the film may be treated with heat (PB). The PB temperature is generally 30 to 200° C., and preferably 50 to 150° C. The organic thin film forming composition may be prepared by, for example, uniformly dissolving the oligothiophene derivative in an appropriate solvent and filtering the solution through a filter with a pore diameter of about 200 nm. As examples of the solvent, chloroform, tetrahydrofuran, chlorobenzene, dichlorobenzene, nitrobenzene, toluene, xylene, mesitylene, 1,2,3,4-tetrahydronaphthalene, dichloromethane, 1,2-dichloroethane, trichloroethane, and 1,1,2,2-chloroethane can be given. These solvents can be used individually or in combination of two or more. The total solid concentration of the organic thin film forming composition is generally 0.1 to 50 mass %, and preferably 1 to 40 mass %.

The exposed underlayer film portion formed by being selectively exposed to light rays through a predetermined pattern contains a reactive acid or base. The acid-dissociable group or base-dissociable group in the organic thin film can be deprotected by the generated acid or base. Therefore, the organic thin film formed on the underlayer film and lower layer and the exposed underlayer film portion being in contact with the organic thin film can chemically bond. No special treatment is needed in order to chemically bond the organic thin film and the exposed underlayer film portion, provided that it is preferable to perform above-mentioned heat-treatment (PB) as needed.

4. Fourth Step:

The fourth step is a step of removing the organic thin film formed on the area other than the exposed underlayer film portion (hereinafter referred to from time to time as "unexposed underlayer film portion").

The organic thin film on the unexposed underlayer film portion can be removed (developed) by treating with a developer generally at 10 to 50° C. for 10 to 200 seconds, preferably at 15 to 30° C. for 15 to 100 seconds, and more preferably at 20 to 25° C. for 15 to 90 seconds. A predetermined resist pattern (negative-tone pattern not irradiated) can be formed in this manner.

As the developer, various organic solvents corresponding to the structure of the organic thin film can be used. In the case of an oligothiophene derivative, an organic solvent such as chloroform, tetrahydrofuran, and the like can be used. A surfactant may be added to the developer ng needed. When forming a resist pattern, a protective film may be provided on the organic thin film in order to prevent an adverse effect of basic impurities and the like which are present in the environmental atmosphere.

EXAMPLES

The present invention is described below in detail by way of examples. Note that the present invention is not limited to the following examples. In the examples, "part(s)" means "part(s) by mass" and "%" means "mass %" unless otherwise indicated.

Synthetic Example 1

Preparation of Underlayer Film Composition (I)

An underlayer film composition (I) containing a hydrolyzate-condensate (resin) of $Si(OCH_3)_4$ and $CH_3Si(OCH_3)_3$ was prepared as follows.

A maleic acid aqueous solution (maleic acid: 0.8 parts, distilled water: 34 parts) was added dropwise to a solution of $Si(OCH_3)_4$ (40 parts) and $CH_3Si(OCH_3)_3$ (8 parts) in 1-ethoxy-2-propanol (117 parts) heated at 60° C. The solution was stirred at 60° C. for four hours and concentrated under reduced pressure to obtain a resin solution (I) (100 parts). The weight average molecular weight (Mw) of the polymer in the resin solution (I) was 2000. Mw of the polymer in the resin solution (I) was measured by gel permeation chromatography (GPC) using monodisperse polystyrene as a standard and using GPC columns (manufactured by Tosoh Corp., G2000HXL×2, G3000HXL×1, G4000HXL×1) at a flow rate of 1.0 ml/minute, using tetrahydrofuran as an eluate, at a column temperature of 40° C. The underlayer film composition (I) (80 parts) was obtained by adding triphenylsulfonium trifluoromethanesulfonate (0.5 parts) to the resin solution (I) (13 parts) and diluting the resulting mixture with 1-ethoxy-2-propanol (13 parts) and distilled water (2 parts).

Synthetic Example 2

Preparation of Underlayer Film Composition (II)

A underlayer film composition (II) containing a polymer (resin) obtained by radical polymerization of acenaphthylene and 5-hydroxymethylacenaphthylene was prepared as follows.

A separable flask equipped with a thermometer was charged with acenaphthylene (8 parts), 5-hydroxymethylacenaphthylene (4 parts), n-butyl acetate (50 parts), and azobisisobutyronitrile (4 parts). The mixture was polymerized at 80° C. for seven hours with stirring. After the reaction, the reaction mixture was diluted with N-butyl acetate (100 parts) and the organic layer was washed with a large amount of a mixed solvent of water and methanol (mass ratio=1:2). The solvent was evaporated to obtain a polymer (II) with Mw of 1500. The resulting polymer (II) (1 part) and triphenylsulfonium trifluoromethanesulfonate (0.1 part) were dissolved in ethyl lactate (20 parts) to obtain the underlayer film composition (II).

Synthetic Example 3

Preparation of Underlayer Film Composition (III)

p-Hydroxyphenyl methacryl anilide (see the following formula (P-1-1)) (90 g), p-t-butoxystyrene (see the following formula (P-1-2)) (30 g), azobisisobutyronitrile (9 g), and 2,4-diphenyl-4-methyl-1-pentene (5 g) were dissolved in methanol. The mixture was polymerized under refluxing (63° C.) for 8 hours. The polymer solution was purified by reprecipitation using a methanol/water mixture, then using an isopropyl alcohol/heptane mixture to obtain a polymer with a monomer molar ratio of p-hydroxyphenyl methacrylanilide/p-t-butoxystyrene=70/30, having Mw of 7000 and Mw/Mn of 1.77. This polymer is designated as a resin (III). The underlayer film composition (III) was obtained by dissolving the resin (III) (1 part), triphenylsulfonium trifluoromethanesulfonate (0.1 part), and, as a crosslinking agent, "NIKALAC MX-750" (manufactured by Sanwa Chemical Co., Ltd.) (0.3 parts) in 1-butanol (20 parts).

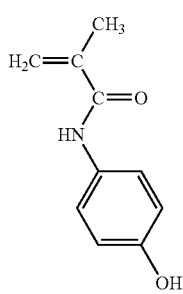

(P-1-1)

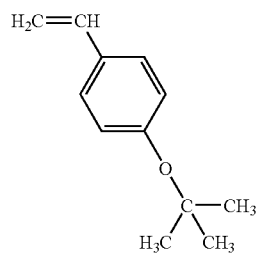

(P-1-2)

Synthetic Example 4

Preparation of Oligothiophene Derivative

A three-neck flask was charged with about 0.25 g (about 0.5 mmol) of $NiCl_2$ (dppp), 5,5'-dibromo-2,2'-bithiophene (201 mmol), and 150 ml of a 1:1:1 mixed solvent of dry ether, dry benzene, and dry THF under nitrogen gas stream. The mixture was cooled over an ice water bath. A separately prepared Grignard reactant of (500 ml) of 2-bromo-3-octylthiophene was slowly added. The mixture was allowed to slowly become room temperature with stirring, followed by stirring while refluxing for three hours. The reaction mixture was washed with water, extracted, and the solvent was evaporated. The resulting crude product was purified by silica gel column chromatography to obtain dioctyl quarter thiophene (4T) at a yield of 70%. The n-butyllithium (100 mmol) was acted on dioctyl quarter thiophene (100 mmol) in THF (500 ml) to lithiate the dioctyl quarter thiophene. After the addition of $CuCl_2$ (200 mmol), the mixture was stirred at room temperature for 24 hours. After evaporating the solvent, the crude product was purified by silica gel column chromatography to obtain a coupling reaction product (8T) at a yield of 25%. The above reaction process is shown in the following reaction equation (44).

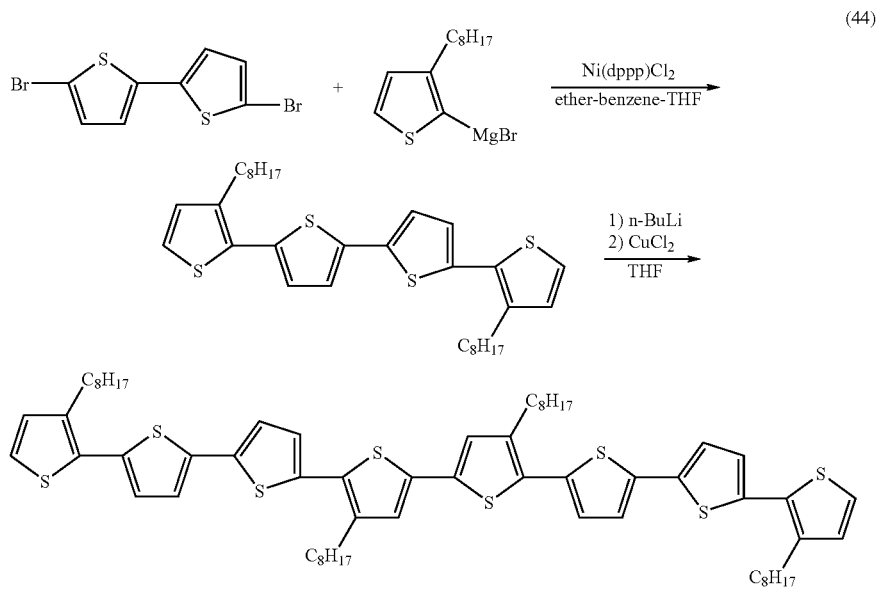

(44)

N-bromosuccinimide (20 mmol) was added to 500 ml of a CMF-CS$_2$ (1:1) solution of 8T (20 mmol) and the mixture was stirred at room temperature for 10 hours to obtain a monobrominated 8T-Br at a yield of 50%. After cooling a THF solution containing chlorotriethoxysilane (5 mmol) with ice under nitrogen gas stream, a separately prepared Grignard reaction agent of 8 T-Br (5 mmol) was carefully added with stirring, whereupon the temperature was slowly returned to room temperature. Then, the mixture was refluxed with stirring for 3 hours. After evaporating the solvent, the reaction product was purified using celite to obtain 8T-Si at a yield of 80%. The 8T-Si is designated as "E-1". The above reaction process is shown in the following reaction equation (45).

The surface analysis was carried out using an X-ray photoelectron spectrometer "Quantum 2000" (manufactured by Ulvac-Phi, Inc.), X-ray output: 25 W (15 kV) under vacuum. An analysis area of 100 μmφ was used. As a result of the surface analysis, sulfur was observed only in the unexposed areas, and was not observed in the exposed areas.

Examples 2 and 3

Underlayer films with a thickness of 80 nm were prepared on silicon wafers in the same manner as in Example 1, except for using the composition for forming the underlayer film composition (II) obtained in Synthetic Example 2 and the

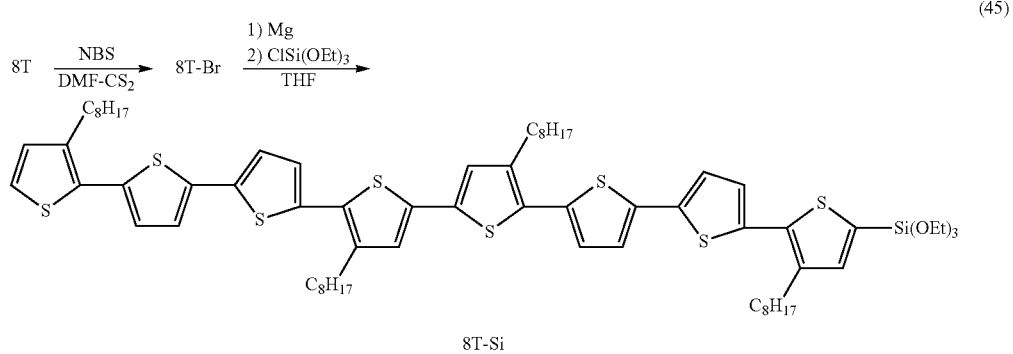

(45)

composition for forming the underlayer film composition (III) obtained in Synthetic Example 3. The compositions for self-organized films were spin coated on the underlayer films of silicon wafer in the same manner as in Example 1. After leaving at the PB temperature shown in Table 1 for one minute, the underlayer film was developed by a Dip method using chloroform at 23° C. for 30 seconds. After washing with purified water, the sample was dried and subjected to surface analysis of the exposed areas and unexposed areas. The analytical results are shown in Table 1.

Comparative Examples 1 and 2

The same composition for self-organized films as used in Example 1 was spin coated on silicon wafers with no underlayer films formed thereon under the PB conditions as shown in Table 1. The self-organized films were irradiated with an electron beam at a dose of 100 μC using a simplified electron beam writer (HL800D manufactured by Hitachi, Ltd., output: 50 KeV, current density: 5.0 A/cm$^2$), and developed by a Dip method using chloroform at 23° C. for 30 seconds. After washing with methanol, then with purified water, the sample was dried and subjected to surface analysis of the exposed areas and unexposed areas. The analytical results are shown in Table 1.

Example 1

The underlayer film composition (I) obtained in "Synthetic Example 1" was applied to a silicon wafer by spin coating and heated on a hot plate at 200° C. for 60 seconds, then on another hot plate at 300° C. for 60 seconds, to obtain an underlayer film with a thickness of 80 nm on a silicon wafer.

The underlayer film formed on the silicon wafer was irradiated with an electron beam at a dose of 100 μC through a mask pattern using a simplified electron beam writer (Type "HL800D" (manufactured by Hitachi, Ltd.), output: 50 KeV, current density: 5.0 A/cm$^2$). The oligothiophene derivative (E-1) (100 parts) shown by the following formula (46), prepared in "Synthetic Example 4", and a solvent (K-1) (chloroform) (2200 parts) were mixed to obtain a homogeneous solution, which was filtered through a membrane filter with a pore size of 200 nm to obtain a composition for self-organized films (solution). The composition for self-organized films was spin-coated on the underlayer film of a silicon wafer. After leaving at the PB temperature shown in Table 1 for one minute, the underlayer film was developed by a Dip method using chloroform at 23° C. for 30 seconds. After washing with methanol, then with water, the sample was dried and subjected to surface analysis of the exposed areas and unexposed areas.

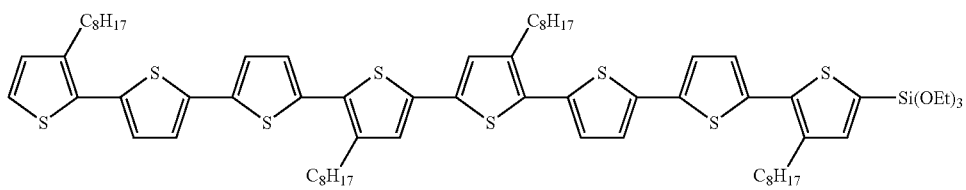

(46)

Comparative Example 3

The same composition for self-organized film as used in Example 1 was spin coated on the underlayer film on the unexposed areas of a silicon wafer under the PB conditions as shown in Table 1. After leaving for one minute under these conditions, the underlayer film was developed by Dip method using chloroform at 23° C. for 30 seconds. After washing with methanol, then with purified water, the sample was dried and subjected to surface analysis of the exposed areas and unexposed areas. The analytical results are shown in Table 1.

TABLE 1

| | Oligothiophene derivative | | Solvent | | | PB conditions | | Sulfur | |
|---|---|---|---|---|---|---|---|---|---|
| | Type | Part | Type | Part | Underlayer film | ° C. | Sec. | Exposed area | unexposed area |
| Exam. 1 | E-1 | 100 | K-1 | 2200 | Observed | 70 | 60 | Observed | Not observed |
| Exam. 2 | E-1 | 100 | K-1 | 2200 | Observed | 70 | 60 | Observed | Not observed |
| Example 3 | E-1 | 100 | K-1 | 2200 | Observed | 70 | 60 | Observed | Not observed |
| Comp. Exam. 1 | E-1 | 100 | K-1 | 2200 | Not observed | 70 | 60 | Not observed | Not observed |
| Comp. Exam. 2 | E-1 | 100 | K-1 | 2200 | Not observed | — | — | Not observed | Not observed |
| Comp. Exam. 3 | E-1 | 100 | K-1 | 2200 | Observed | 70 | 60 | — | Not observed |

As clear from the results shown in Table 1, when a self-organized film was applied on a selectively exposed underlayer film, sulfur was observed only in unexposed areas, and was not observed in the exposed areas (Examples 1 to 3). On the other hand, sulfur was not observed in both the exposed and unexposed areas when there was no underlayer film (Comparative Examples 1 and 2). Even in the case in which there was an underlayer film, sulfur was not observed when the underlayer film was not exposed (Comparative Example 3). Based on the above results, the oligothiophene derivatives were confirmed to be selectively adsorbed only in the exposed areas of the underlayer film. It is possible to form micro patterns by appropriately selecting the structure of oligothiophene derivatives.

INDUSTRIAL APPLICABILITY

The method for forming a pattern of the present invention is very useful as a process for manufacturing semiconductor chips which are expected to be miniaturized in the future.

The invention claimed is:

1. A method for forming a pattern, comprising:
   (1) a step of forming an underlayer film containing (A) a radiation-sensitive acid generator capable of generating an acid upon exposure to radiation rays or (B) a radiation-sensitive base generator capable of generating a base upon exposure to radiation rays on a substrate;
   (2) a step of irradiating the underlayer film with radiation rays through a mask with a predetermined pattern to obtain an exposed underlayer film portion having been selectively exposed to radiation rays through the predetermined pattern;
   (3) a step of forming (C) an organic thin film on the underlayer film so as to attain chemical bonding of the exposed underlayer film portion to the organic thin film formed on the exposed underlayer film portion; and;
   (4) a step of removing the organic thin film formed on areas of the underlayer film other than the exposed underlayer film portion, wherein the organic thin film contains an oligothiophene derivative,
   wherein the oligothiophene derivative contains an acid-dissociable group or a base-dissociable group, and
   wherein the acid-dissociable group contained in the oligothiophene derivative is shown by the following formula (6), $$-Si(OR^{14})_3 \qquad (6)$$

wherein $R^{14}$s may be the same or different and each independently represents a substituted or unsubstituted alkyl group having 1 to 5 carbon atoms, an aryl group having 6 to 14 carbon atoms, an allyl group, a glycidyl group, or a hydrogen atom.

2. The method for forming a pattern according to claim 1, wherein the underlayer film further contains at least one hydrolyzate and/or condensate selected from the group consisting of (D) a compound (D-1) shown by the following formula (1) and a compound (D-2) shown by the following formula (2), $$R^1_a Si(OR^2)_{4-a} \qquad (1)$$

wherein $R^1$ represents a hydrogen atom, a fluorine atom, or a monovalent organic group, $R^2$ represents a monovalent organic group, and a represents an integer of 0 to 2, $$R^3_b(R^4O)_{3-b}Si-(R^7)_d-Si(OR^5)_{3-c}R^6_c \qquad (2)$$

wherein $R^3$ to $R^6$ may be the same or different and each represents a substituted or unsubstituted alkyl group, aryl group, allyl group, or glycidyl group, b and c may be the same or different and represent an integer of 0 to 2, $R^7$ represents an oxygen atom or a "—$(CH_2)_n$—"-bond, d represents 0 or 1, and n represents an integer of 1 to 6.

3. The method for forming a pattern according to claim 1, wherein the underlayer film further contains (E) a polymer which has at least one repeating unit selected from the group consisting of a repeating unit (E-1) shown by the following formula (3) and a repeating unit (E-2) shown by the following formula (4), and has a polystyrene-reduced weight average molecular weight (Mw) measured by the gel permeation chromatography of 500 to 500,000,

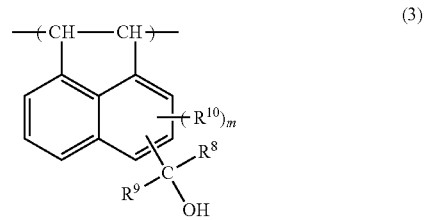

(3)

(4)
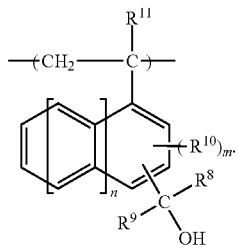

(5)
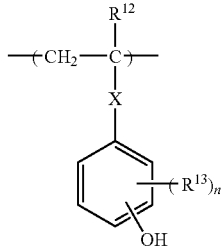

wherein $R^8$ and $R^9$ individually represent a hydrogen atom, an alkyl group having 1 to 3 carbon atoms, or an aryl group, $R^{10}$ represents an alkyl group having 1 to 3 carbon atoms, a vinyl group, an allyl group, or an aryl group, $R^{11}$ represents a hydrogen atom or a methyl group, n represents 0 or 1, and m represents an integer of 0 to 2.

4. The method for forming a pattern according to claim 1, wherein the underlayer film further contains (F) a polymer which has a repeating unit shown by the following formula (5) and has a polystyrene-reduced weight average molecular weight (Mw) measured by the gel permeation chromatography of 500 to 500,000, wherein $R^{12}$ represents a hydrogen atom or a methyl group, $R^{13}$ represents an alkyl group having 1 to 3 carbon atoms, a vinyl group, an allyl group, or an aryl group, X represents a single bond, —C(.dbd.O)—O—, or —C(.dbd.O)—NH—, and n represents an integer of 0 to 4.

5. A composition for forming (C) an organic thin film used in the method for forming a pattern according to claim 1, comprising (G) an oligothiophene derivative and (H) a solvent.

* * * * *